(12) United States Patent
Chen et al.

(10) Patent No.: US 11,759,274 B2
(45) Date of Patent: Sep. 19, 2023

(54) SURGICAL DEVICE AND METHOD THEREOF

(71) Applicant: POINT ROBOTICS (SINGAPORE) PTE. LTD., Singapore (SG)

(72) Inventors: Chih-Wei Chen, Hsinchu (TW); Hao-Kai Chou, Hsinchu (TW); Xiu-Yun Xiao, Hsinchu (TW)

(73) Assignee: POINT ROBOTICS (SINGAPORE) PTE. LTD., Singapore (SG)

( * ) Notice: Subject to any disclaimer, the term of this patent is extended or adjusted under 35 U.S.C. 154(b) by 428 days.

(21) Appl. No.: 17/210,532

(22) Filed: Mar. 24, 2021

(65) Prior Publication Data

US 2022/0304756 A1 Sep. 29, 2022

(51) Int. Cl.
*A61B 34/30* (2016.01)
*A61B 34/00* (2016.01)
*A61B 90/00* (2016.01)

(52) U.S. Cl.
CPC .............. *A61B 34/70* (2016.02); *A61B 34/25* (2016.02); *A61B 90/39* (2016.02); *A61B 2034/731* (2016.02)

(58) Field of Classification Search
CPC ......... A61B 34/00; A61B 34/30; A61B 34/70; A61B 34/25; A61B 90/00; A61B 90/39; A61B 2034/731; A61B 19/201; A61B 19/203; A61B 19/5244

See application file for complete search history.

(56) References Cited

U.S. PATENT DOCUMENTS

| 8,912,746 B2 * | 12/2014 | Reid | A61B 34/30 |
| | | | 318/560 |
| 2020/0397499 A1 * | 12/2020 | Takahashi | A61B 34/30 |

* cited by examiner

*Primary Examiner* — Vi X Nguyen
(74) *Attorney, Agent, or Firm* — Li & Cai Intellectual Property Office

(57) ABSTRACT

A surgical device for retaining a tool, the surgical device comprises a multi-axis manipulator configured to generate relative movement between a moving end and a stationary end thereof; a housing fixed to the stationary end of the manipulator; a motor configured to rotate the tool by a rotating interface when the tool is retained to the rotating interface; an adaptor connected to the manipulator and in orientational fixation to the moving end of the manipulator, the adaptor being configured to move with the moving end, and the adaptor comprises a tool stopper disposed therein, wherein the tool stopper is configured to catch the tool if the tool is dropped from the rotating interface; a tool head latchless interface exposed to a channel of the adaptor and configured to provide attraction force within the channel for retaining the tool to the rotating interface.

21 Claims, 23 Drawing Sheets

- Receiving a third confirmation by the surgical device — S201

- Sending a third signal to a tool head latchless interface in the surgical device — S202

- Providing repulsion force by the tool head latchless interface according to the third signal — S203

- Moving a tool over a tool stopper in a channel of an adaptor of the surgical device by repulsion force from the tool head latchless interface — S204

- Ejecting the tool from the channel of the adaptor to a tool box by repulsion force from the tool head latchless interface — S205

Fig. 17

```
┌─────────────────────────────────────────────────────────┐
│ Detecting leakage of electricity by an electrical leakage│──— S301
│        feedback circuit in the surgical device          │
└─────────────────────────────────────────────────────────┘

┌─────────────────────────────────────────────────────────┐
│     Sending a fourth signal to a tool head latchless    │
│ interface that is providing attraction force in a channel│──— S302
│ of an adaptor of the surgical device after detection of │
│                  leakage of electricity                 │
└─────────────────────────────────────────────────────────┘

┌─────────────────────────────────────────────────────────┐
│ Stop providing attraction force in the channel by the   │──— S303
│ tool head latchless interface according to the fourth   │
│                         signal                          │
└─────────────────────────────────────────────────────────┘

┌─────────────────────────────────────────────────────────┐
│ Catching a tool dropping from a motor after cease of    │──— S304
│  attraction force by a tool stopper in the channel      │
└─────────────────────────────────────────────────────────┘

┌─────────────────────────────────────────────────────────┐
│   Sending a fifth signal to the tool head latchless     │──— S305
│ interface after leakage of electricity is not detected by│
│         the electrical leakage feedback circuit         │
└─────────────────────────────────────────────────────────┘

┌─────────────────────────────────────────────────────────┐
│  Providing attraction force by the tool head latchless  │──— S306
│        interface according to the fifth signal          │
└─────────────────────────────────────────────────────────┘

┌─────────────────────────────────────────────────────────┐
│  Pulling the tool from the tool stopper toward the      │
│ motor and retaining the tool to the motor by attraction │──— S307
│     force from the tool head latchless interface        │
└─────────────────────────────────────────────────────────┘
```

Fig. 18

SURGICAL DEVICE AND METHOD THEREOF

FIELD

The present disclosure generally relates to a surgical device and a method thereof. More particularly, the present disclosure relates to the surgical device that can mount a tool by contactless force.

BACKGROUND

In a surgical environment, one issue that every surgeon and medical personnel may concern is contamination. Generally speaking, most surgery requires multiple surgical operations, for example, cutting, removing, and suturing, etc. And, each of the surgical operation often requires a specific surgical tool, such as a scalpel for cutting an incision. Therefore, a surgeon needs to lay his/her hand on different surgical tools through a surgery. Though many surgical tools are disposable for one-time use, touching multiple surgical tools can still increase chances of contamination transferred from a patient's blood, tissue, purulence, and other source of contamination. Because it is the surgeon that is touching the tool, contamination can be transferred to surgical gloves on the surgeon's hand.

These days, some surgery is conducted with semi-automatic surgical devices for high accuracy and stable operation. However, the same problem of contamination transfer persists because the surgeon or medical personnel is also required to mount and dismount multiple surgical tools to or from the surgical device, respectively. Although proper sterilization can be carried out between the changing of surgical tools, the risk of contamination transfer is still not eliminated.

The present disclosure provides a surgical device that can mount or dismount a surgical tool without the surgeon or medical personnel grabbing the surgical tool.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

FIG. 17 shows a method of a surgical device according to one embodiment of the present disclosure.

FIG. 18 shows a method of a surgical device according to one embodiment of the present disclosure.

DETAILED DESCRIPTION

Figure 1:
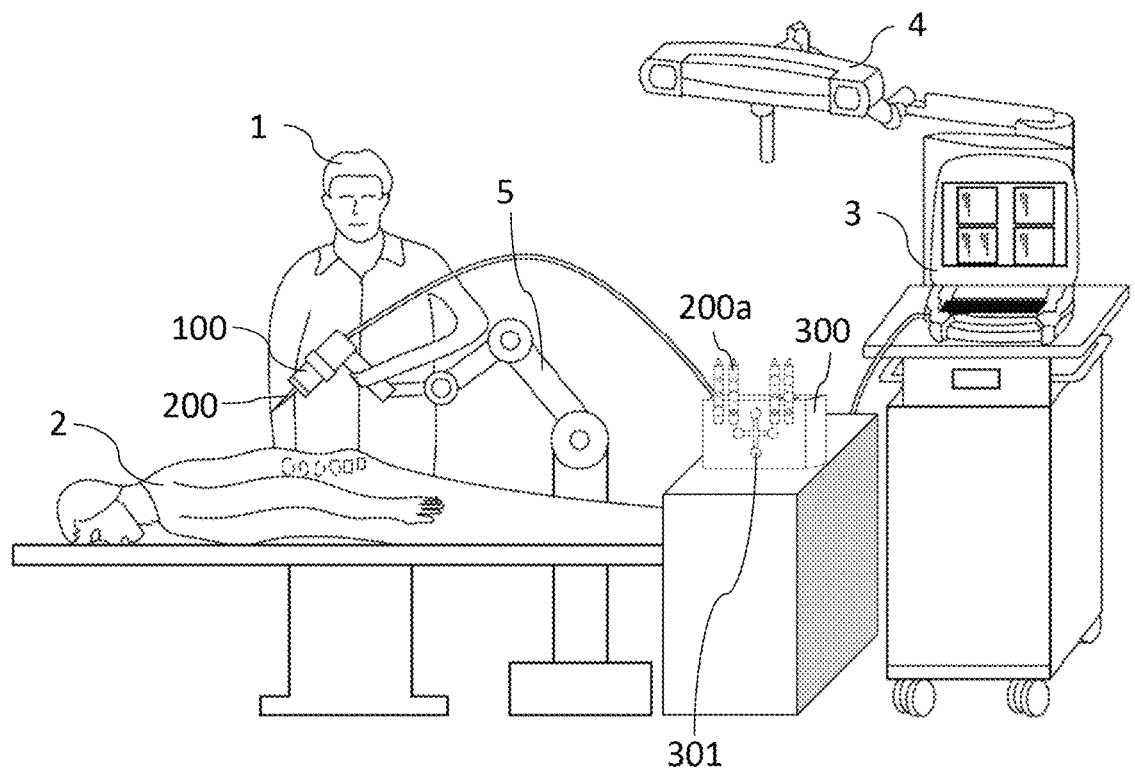
FIG. 1 illustrates an isometric view of a surgical environment according to one embodiment of the present disclosure.

It will be appreciated that for simplicity and clarity of illustration, where appropriate, reference numerals have been repeated among the different figures to indicate corresponding or analogous elements. In addition, numerous specific details are set forth to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale, and the proportions of certain parts may be exaggerated to better illustrate details and features of the present disclosure.

It should be noted that, the term "connect" or "couple" can either mean directly in touch or indirectly in touch.

FIG. 1 illustrates a surgical environment according to one embodiment of the present disclosure. In the surgical environment, a surgeon 1 can hold a surgical device 100 connected to a robotic arm 5 to conduct a surgery to a patient 2. A surgical computer 3 is connected to the robotic arm 5 and a tracker 4. As such, the surgical computer 3 is configured to receive positional information from the tracker 4 in order to navigate movement of the surgical device 100 by the robotic arm 5 accordingly. More specifically, the tracker 4 comprises optical sensor and is configured to receive optical signal from fiducial markers (not shown) fixed to the surgical device 100; the tracker 4 is configured to generate positional information according to the optical signal, so the position of the surgical device 100 can be known to the surgical computer 3. One end of the surgical device 100 is connected to a tool 200 for surgical operations of the surgery to be conducted. In the case where multiple different tools are required in a surgery, the tool 200 on the surgical device 100 can be swapped with another tool 200a in a tool box 300. Moreover, most of time a surgery involves multiple surgical operations that can only be completed by different tools, and thus tool swapping is a frequent action during a surgery. Tool swapping is usually performed by a surgeon or a medical assistant using his/her hand. Of course, whoever swapping a tool can wear a sterilized glove, but this does not avoid contamination from a patient's blood or tissue that can transfer to the glove from the tool being swapped, from which possibility of contamination come. In the present disclosure, the surgical device 100 is configured to swap between different tools without one physically touching the tools directly, and therefore chances of contamination can be reduced.

Figure 2:
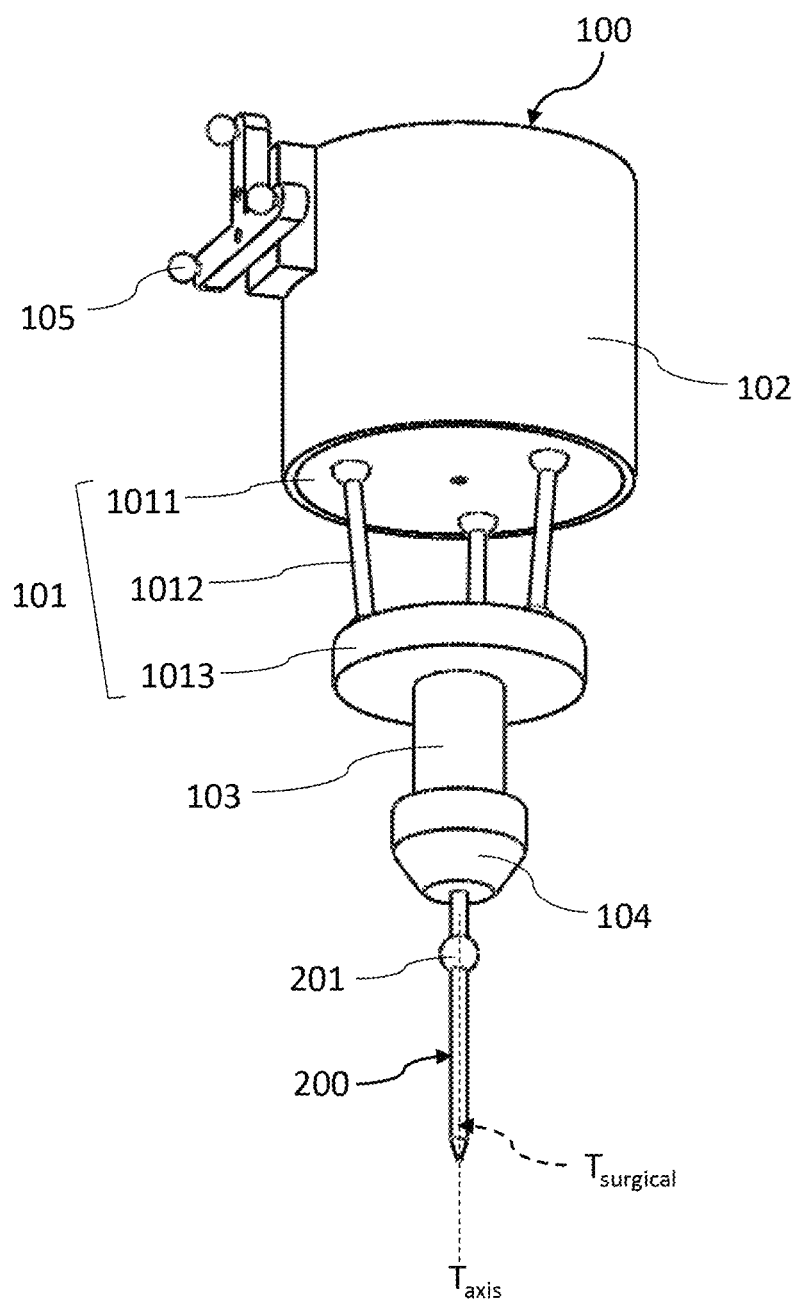
FIG. 2 illustrates an isometric view of a surgical device according to one embodiment of the present disclosure.

FIG. 2 illustrates an isometric view of a surgical device according to one embodiment of the present disclosure. In FIG. 2, a surgical device 100 comprises a multi-axis manipulator 101, a housing 102, a motor 103, and an adaptor 104. The multi-axis manipulator 101 comprises a stationary end 1011, a moving end 1013, and multiple joints 1012 connecting the moving end 1013 to the stationary end 1011. The multi-axis manipulator 101 is configured to generate relative movement between the moving end 1013 and the stationary end 1011 by moving the multiple joints 1012. The housing 102 is fixed to the stationary end 1011 of the multi-axis manipulator 101, so the moving end 1013 can be moved relative to the housing 102 when the housing 102 is connected to the robotic arm 5 in FIG. 1. The motor 103 is fixed between the moving end 1013 and the adaptor 104, and as such the motor 103 and the adaptor 104 are configured to move with the moving end 1013. The adaptor 104 is configured to receive a rotating interface (not shown) of the motor 103 and a tool 200, and the tool 200 is retained to the rotating interface in the adaptor 104, so the motor 103 is configured to drive the tool 200 to rotate by the rotating interface. In one embodiment of the present disclosure, the adaptor 104 is in orientation fixation to the moving end 1013, for example the orientation of the adaptor 104 with respect to the moving end 1013 remains unchanged as the multi-axis manipulator 101 moves. For example, when the moving end 1013 moves, for example: up/down, forward/backward, left/right, roll, yaw, and pitch, the adaptor 104 moves accordingly. For another example, the adaptor 104 has a first axis, and the moving end 1013 has a second axis in a specific relation (e.g. parallel, intersecting, perpendicular, coincide, etc.) to the first axis, the specific relation is maintained between the adaptor 104 and the moving end 1013. The motor 103 is configured to generate torque by rotating the rotating interface, and the rotating interface is configured to rotate continuously for surgical operation such as drilling or by a specific degree for surgical operation such as implant placement or nerve retraction. For example, the motor 103 can be step motor or servo motor to realize turning the rotating interface by a specified degree. For surgical operation that requires the tool 200 moving in forms other than rotation, the multi-axis manipulator 101 is configured to achieve that by driving the moving end 1013 with the multiple joints 1012; for example, the multiple joints 1012 are configured to move the moving end 1013 up and down in FIG. 2 for surgical operation such as piling. In one embodiment, the multi-axis manipulator 101 is a parallel manipulator which has many advantages compared to a serial manipulator, for example: less inertia force, higher stiffness, well defined and unique direct force transformation, precise positioning, etc.

Figure 3:
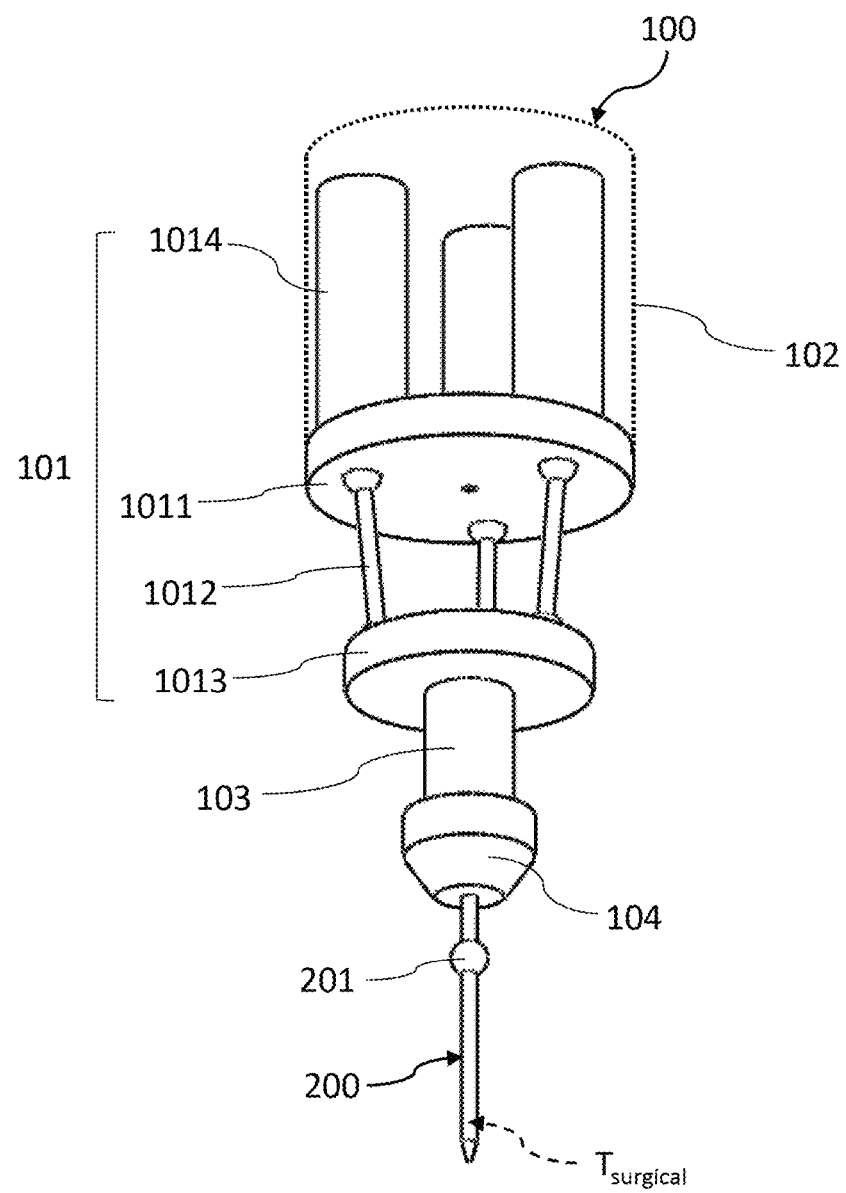
FIG. 3 illustrates an isometric view of a surgical device according to one embodiment of the present disclosure.
Figure 4:
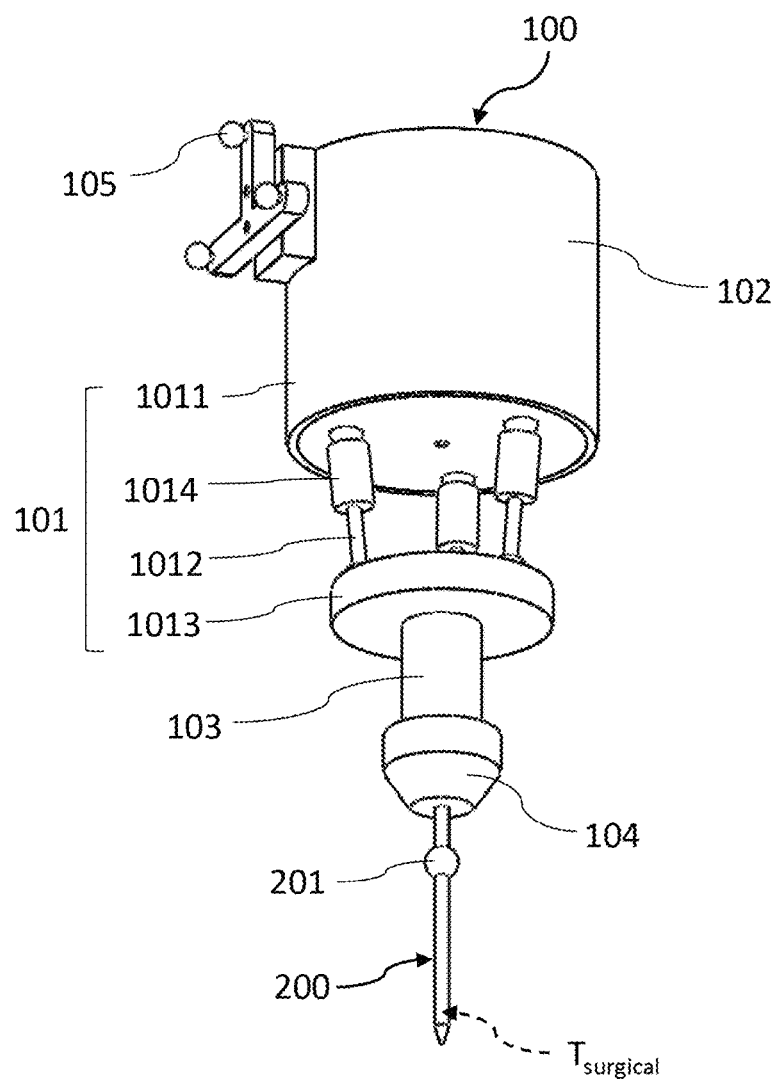
FIG. 4 illustrates an isometric view of a surgical device according to one embodiment of the present disclosure.

In one embodiment of the present disclosure, FIG. 3 illustrates the multi-axis manipulator 101 of the surgical device 100 further comprises multiple linear motors 1014 connected to the multiple joints 1012 and configured to drive the joints 1012 correspondingly. More specifically, one joint 1012 connected to a slider of one linear motor 1014 can be elongated and shortened as the slider moves, and the moving end 1013 fixed to the multiple joints 1012 is moved by this way. In regard to the aforementioned piling surgical operation, the multiple linear motor 1014 are configured to drive all the joints 1012 to elongate and shorten together in a repeating manner, so the tool 200 is configured to move back and forth with the moving end 1013 in relation to a patient under the piling surgical operation. In FIG. 3, the multiple linear motors 1014 can be accommodated by the housing 102 which is shown translucent for clear description. In another embodiment of the present disclosure, the multiple linear motors 1014 is disposed between the stationary end 1011 and the moving end 1013 of the multi-axis manipulator 101 as shown in FIG. 4. In this case, spaces occupied by the multiple linear motors 1014 in the housing 102 can be saved for other components. Furthermore, exposing the multiple linear motors 1014 is beneficial to maintenance or repair thereof. Though the multi-axis manipulator 101 is driven by the multiple linear motors 1014 in the embodiments illustrated in FIG. 3 and FIG. 4, the linear motors 1014 can be substituted by a combination of servo/stepped motor, lead/ball screws, and nuts, as long as linear motion can be provided to cause each of the joints 1012 of the multi-axis manipulator 101 to elongate and shorten.

Figure 5:
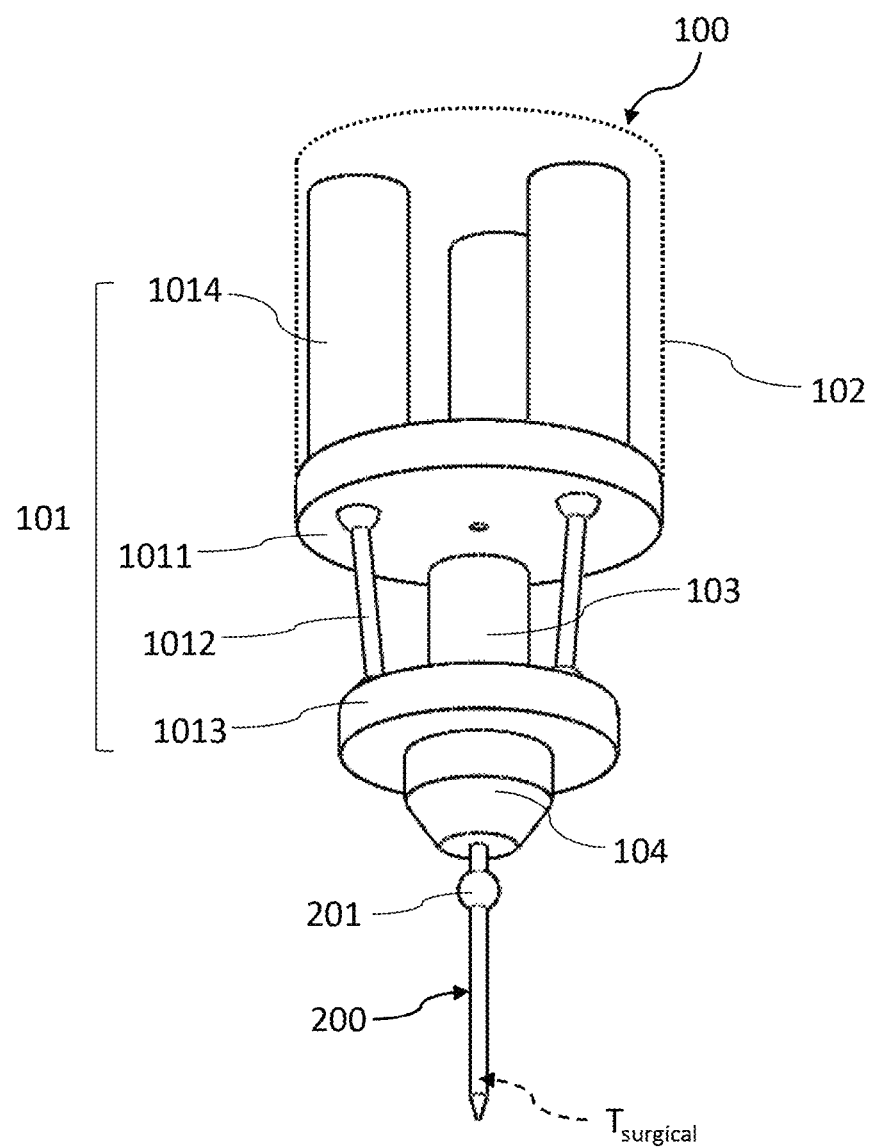
FIG. 5 illustrates an isometric view of a surgical device according to one embodiment of the present disclosure.
Figure 6:
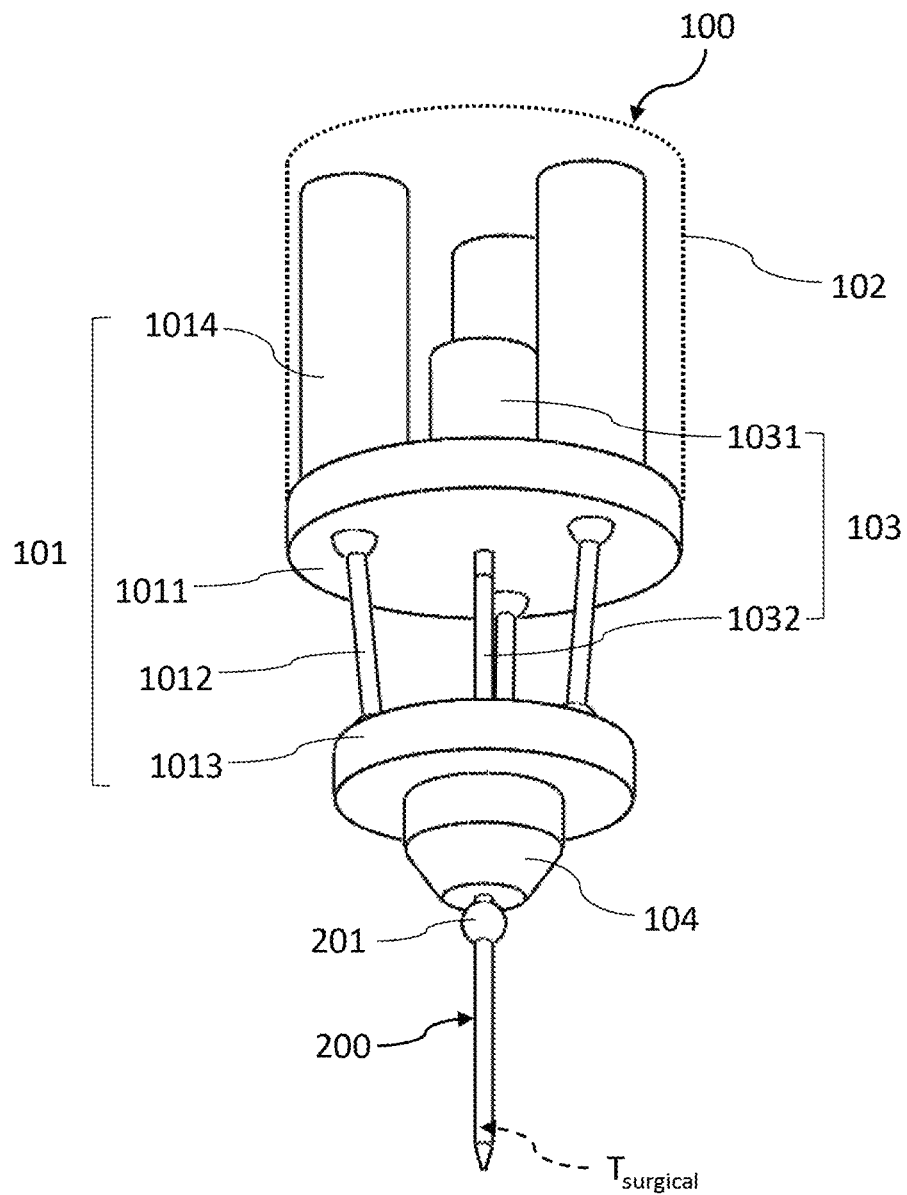
FIG. 6 illustrates an isometric view of a surgical device according to one embodiment of the present disclosure.

FIG. 5 illustrates an arrangement of motor 103 according to one embodiment of the present disclosure. In FIG. 5, the motor 103 is disposed at least partially between the stationary end 1011 and the moving end 1013 of the multi-axis manipulator 101, as such the surgical device 100 in FIG. 5 is shorter in length comparing to the surgical device 100 in FIG. 2. In this embodiment, the motor 103 is configured to deliver torque to the tool 200 for rotating the tool 200 just like aforementioned embodiments. Moreover, partially or fully incorporating the motor 103 into the moving end 1013 may increase stability of the multi-axis manipulator 101 while the motor 103 delivering torque, thereby precision of surgery can be increased. In another embodiment of the present disclosure, the same concept is further applied by incorporating the motor 103 into the housing 102 as shown in FIG. 6. It should be noted that, in both FIG. 5 and FIG. 6, the housing 102 is shown translucent for clear description. The motor 103 comprises a main body 1031 and a rotating interface 1032, and the main body 1031 is disposed in the housing 102 between the multiple linear motors 1014, so the adaptor 104 and the main body 1031 are disposed on different side of the multi-axis manipulator 101. In this embodiment, the rotating interface 1032 is in elongated shape with two ends, and one end is fixed to a rotor in the main body 1031 while the other end is arranged in the adaptor 104 for connecting and rotating the tool 200. In other words, the rotating interface 1032 is configured to transfer torque provided by the main body 1031 to the tool 200. For the main body 1031 being disposed in the housing 102, the vibrational interference from rotating rotor in the motor 103 is greatly reduced at a surgical end $T_{surgical}$ of the tool 200 that is in proximity to a patient under a surgical operation. Furthermore, the multi-axis manipulator 101 is no longer required to bear the weight of the motor 103, hence longer usage life. In addition, less weight at the moving end 1013 of the multi-axis manipulator 101 also facilitates better control of the multi-axis manipulator 101 because of less inertia, thus less settling time of the moving end 1013. As a result, the surgical end $T_{surgical}$ of the tool 200 that conducts a surgical operation can settle faster as well.

Referring back to FIG. 2, the surgical device 100 further comprises at least one device marker 105 fixed thereon; the tool 200 comprises a tool marker 201 disposed thereon. For the present disclosure, a tool axis $T_{axis}$ is defined between two ends of the tool 200 in which one end (also called adaptor end $T_{adaptor}$) is disposed in the adaptor 104 while the other end (also called surgical end $T_{surgical}$) is for conducting a surgical operation. In one embodiment, the tool marker 201 is disposed coaxially to the tool axis $T_{axis}$ of the tool 200, so rotation of the tool 200 caused by the motor 103 does not affect positional information of the tool marker 201. Both the device marker 105 and the tool marker 201 are fiducial markers that can be tracked by the tracker 4 in FIG. 1, in other words, the device marker 105 and the tool marker 201 are configured to reflect or emit optical signal to the tracker 4 in which positional information of the surgical device 100 and the tool 200 can be generated. Though the device marker 105 is not shown in FIG. 3, FIG. 5, and FIG. 6, it is omitted just for clarity of visual illustration. Since the tool 200 may be moved by the multi-axis manipulator 101, and the surgical device 100 including the multi-axis manipulator 101 can further be moved by the robotic arm 5, tracking the device marker 105 and the tool marker 201 by the tracker 4 allows the surgical computer 3 to know the position of the surgical device 100, the tool 200, and a relative position between the surgical device 100 and the tool 200. In this way, the basic requirement of fully automated tool swapping, which is knowing the position of the surgical device 100 and the tool 200, is satisfied. For example, the surgical computer 3 is configured to navigate the movement of the surgical device 100 to approach the tool 200 according to the positional information thereof, hence mounting the tool 200 to the surgical device 100 without grabbing the tool 200 by one's hand. However, to facilitate fully automated tool swapping, not only the position information of the surgical device 100 and the tool 200, but also an ability of automatically mounting the tool 200 to the surgical device 100 is needed. This will be further described in FIG. 7 to FIG. 13 which shows the cross-sectional view of the adaptor 104, part of the motor 103, and part of the tool 200.

Figure 7:
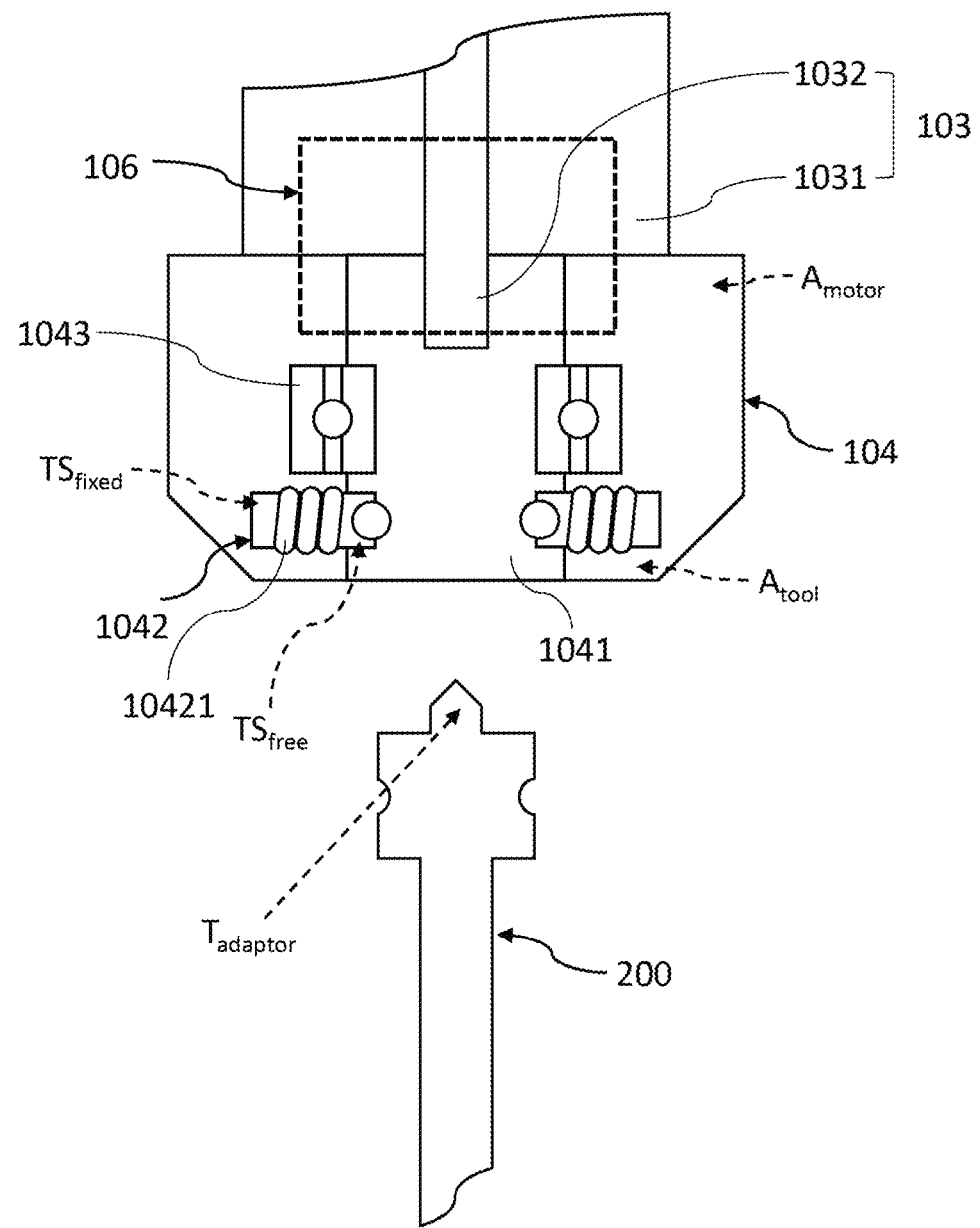
FIG. 7 illustrates a cross-sectional view around an adaptor according to one embodiment of the present disclosure.

FIG. 7 to FIG. 13 illustrate a partial cross-sectional view of the surgical device 100 around an adaptor 104 according to one embodiment of the present disclosure. As shown in FIG. 7, the adaptor 104 comprises a motor end $A_{motor}$, a tool end $A_{tool}$, and a channel 1041 extending between the motor end $A_{motor}$ and the tool end $A_{tool}$, and a tool stopper 1042 disposed between the motor end $A_{motor}$ and the tool end $A_{tool}$. The channel 1041 is configured to receive the rotating interface 1032 from the motor end $A_{motor}$ and to receive the tool 200 from the tool end $A_{tool}$, and the rotating interface 1032 is configured to connect to the tool 200 in the channel 1041. The surgical device 100 further comprises a tool head latchless interface 106 exposed to the channel 1041 and configured to provide attraction force within the channel 1041 for retaining the tool 200 to the rotating interface 1032, thereby mounting the tool 200 to the surgical device 100. In one embodiment, the device marker 105 and the tool marker 201 form a spatial pattern recognizable to the tracker 4, and coordinates (e.g. cartesian coordinates) of the recognized spatial pattern is sent to the surgical computer 3 for determination, whereby proper retention of the tool 200 to the rotating interface 1032 is determined when the coordinates of the spatial pattern matches a specific geometrical relationship saved in the surgical computer 3. Attraction force can be in the form of gas pressure, magnetic force, or the like. It should be noted that the tool head latchless interface 106 is illustrated without physical structure in FIG. 7 to FIG. 10 for clarity of visual illustration, which emphasizes on the ability of providing invisible force that facilitates mounting the tool 200 without grabbing it with hand, and the tool head latchless interface 106 will be further described in detail in FIG. 11 and FIG. 12.

Figure 8:
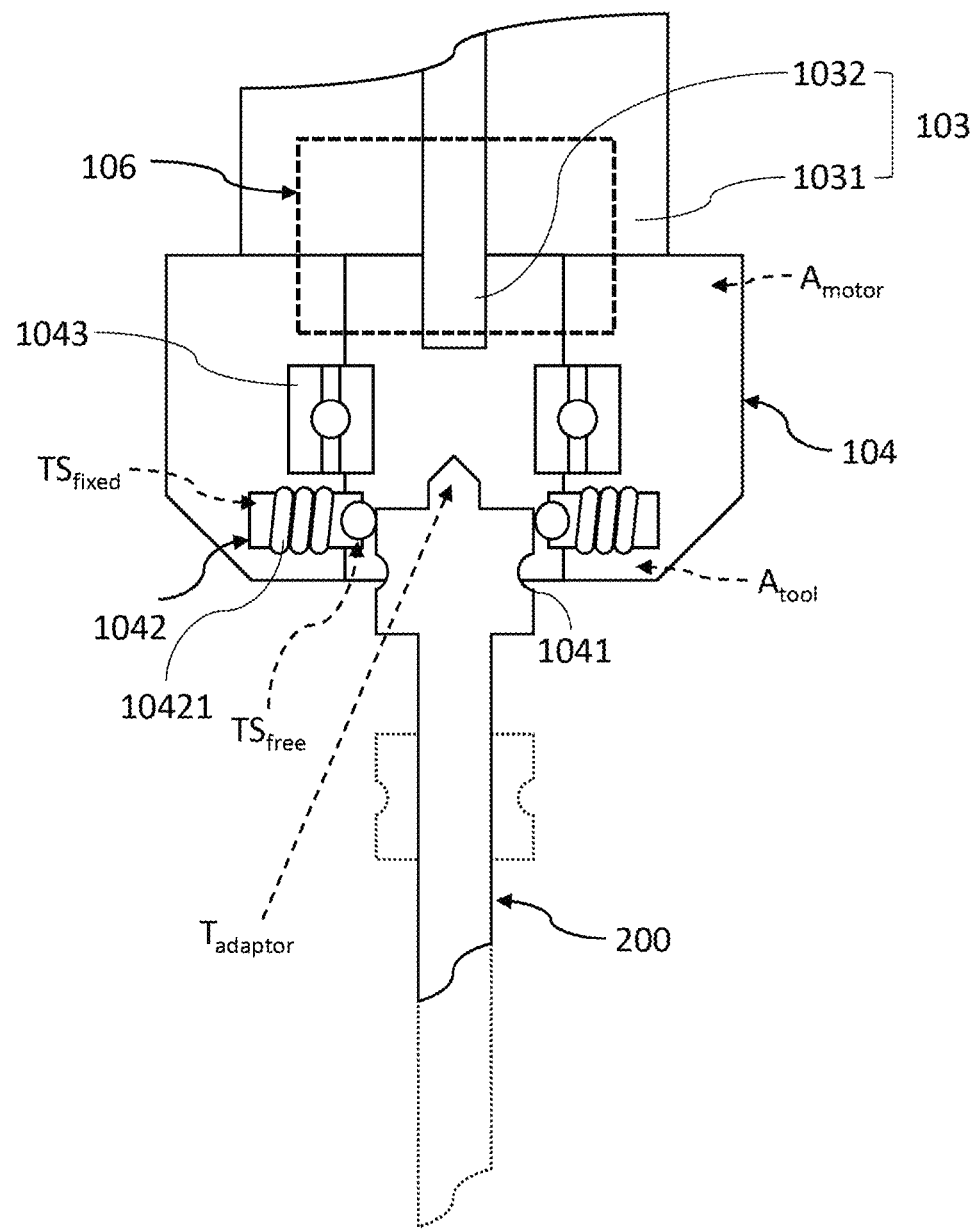
FIG. 8 illustrates a cross-sectional view around an adaptor according to one embodiment of the present disclosure.

In one embodiment of the present disclosure, the tool head latchless interface 106 is configured to pulls(draws) the tool 200 over the tool stopper 1042 by attraction force provided. As shown in FIG. 8, the tool 200 is pulled from outside to inside of the channel 1041 of the adaptor 104. The tool stopper 1042 comprises a fixed end $TS_{fixed}$ fixed to the adaptor, a free end $TS_{free}$ extending into the channel, and a resilient unit 10421 disposed between the free end $TS_{free}$ and the fixed end $TS_{fixed}$. The resilient unit 10421 allows the free end $TS_{free}$ urged toward the fixed end $TS_{fixed}$ by the tool 200 to be reset when the tool 200 overcome the tool stopper 1042. The tool stopper 1042 further comprises a roller ball 10422 at its free end $TS_{free}$, and the roller ball 10422 is configured to avoid the tool 200 from wearing by the tool stopper 1042 when the tool 200 passes over the free end $TS_{free}$. After the tool 200 passing over the free end on its way to be retained by the rotating interface 1032, the tool stopper 1042 can be kept distant from the tool 200, thus not interfering with rotation of the tool 200.

Figure 9:
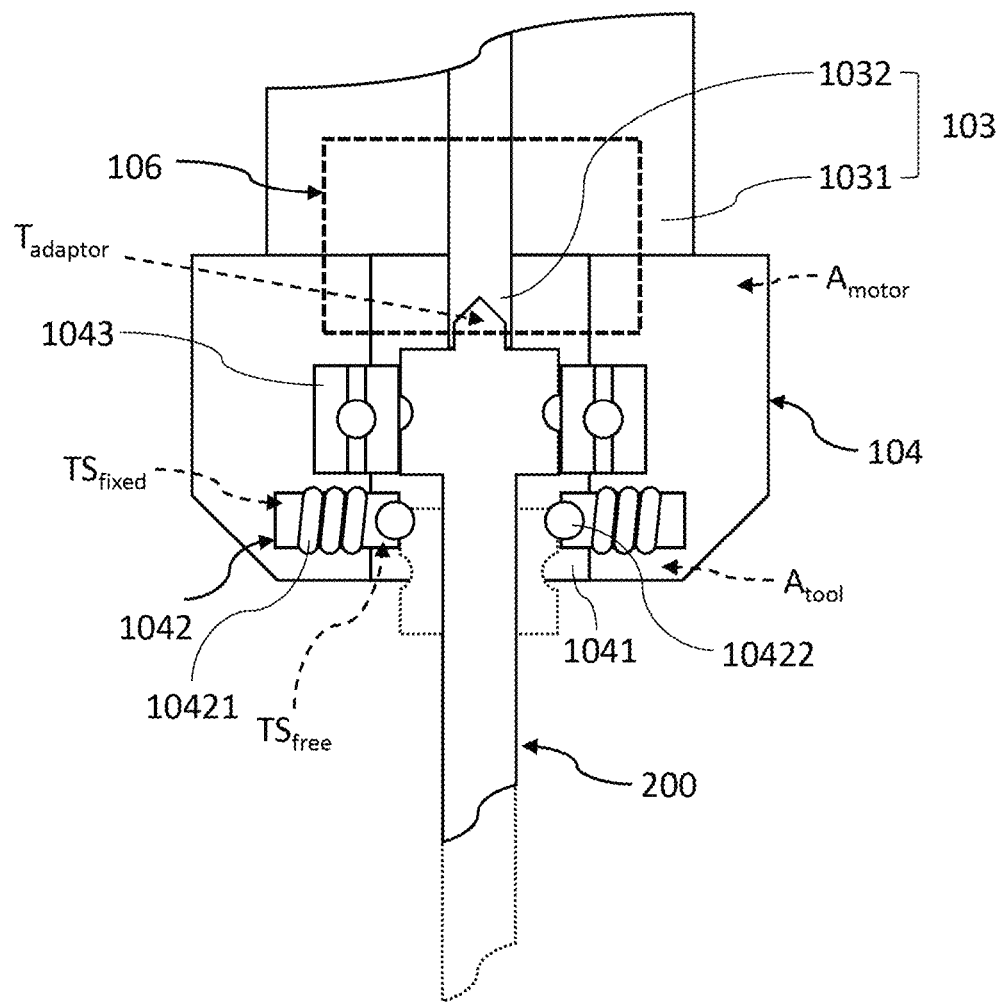
FIG. 9 illustrates a cross-sectional view around an adaptor according to one embodiment of the present disclosure.

As the tool head latchless interface 106 continues providing attraction force, the tool 200 is further pulled into the channel 1041 as shown in FIG. 9. Therefore, the tool 200 is connected to the rotating interface 1032 of the motor 103. As such, the tool stopper 1042 is no longer urged by the tool 200, and hence the free end $TS_{free}$ is reset by the resilient unit 10421 to its original position. Furthermore, as long as the tool head latchless interface 106 is providing attraction force, an adaptor end $T_{adaptor}$ of the tool 200 can be retained to the rotating interface 1032 in the channel 1041 of the adaptor 104. In one embodiment of the present disclosure, the adaptor end $T_{adaptor}$ of the tool 200 comprises at least two faces (e.g., a planar surface) that are structurally complementary to the rotating interface 1032, so the rotating interface 1032 is configured to rotate the tool 200 by torque provided from main body 1031 of the motor 103. The adaptor 104 further comprises a bearing 1043 exposed to the channel 1041 and disposed between the motor end $A_{motor}$ and the tool end $A_{tool}$. The bearing 1043 is configured to surround the tool 200 retained to the rotating interface 1032, thereby touching the tool 200 in addition to the rotating interface 1032, so a contact area between the tool 200 and the adaptor 104 is increased, and thus facilitating stable rotation thereof in the channel 1041 of the adaptor 104. In one embodiment of the present disclosure, when the tool 200 is retained by the tool head latchless interface 106 to the rotating interface 1032, the tool 200 is just in touch with the bearing 1043 other than the tool head latchless interface 106 and the rotating interface 1032, thereby reducing friction acting upon the tool 200 while the tool 200 is rotating. In other words, the tool 200 is in physical contact only with the tool head latchless interface 106, the rotating interface 1032, and the bearing 1043. In another embodiment, the roller ball 10422 at the free end $TS_{free}$ is designed to touch the tool 200 when the tool 200 is retained to the rotating interface 1032, such that further increases the stability of rotation of the tool 200.

In one embodiment, the tool head latchless interface 106 is further configured to provide repulsion force. Similar to attraction force, repulsion force can be in the form of gas pressure, magnetic force, or the like that can be provided to the tool 200 without physically touching it, thereby facilitating the tool 200 to be dismounted without pulling it with hand. When the tool head latchless interface 106 provides repulsion force, the tool 200 is pushed(thrust) over the tool stopper 1042, as such the tool is moved from inside to outside of the channel 1041 of the adaptor 104 and separated from the rotating interface 1032, thereby dismounting the tool 200 from the surgical device 100. In regard to the process of mounting the tool 200 as shown from FIG. 7 to FIG. 9, dismounting the tool 200 is basically an inversed process thereof.

Figure 10:
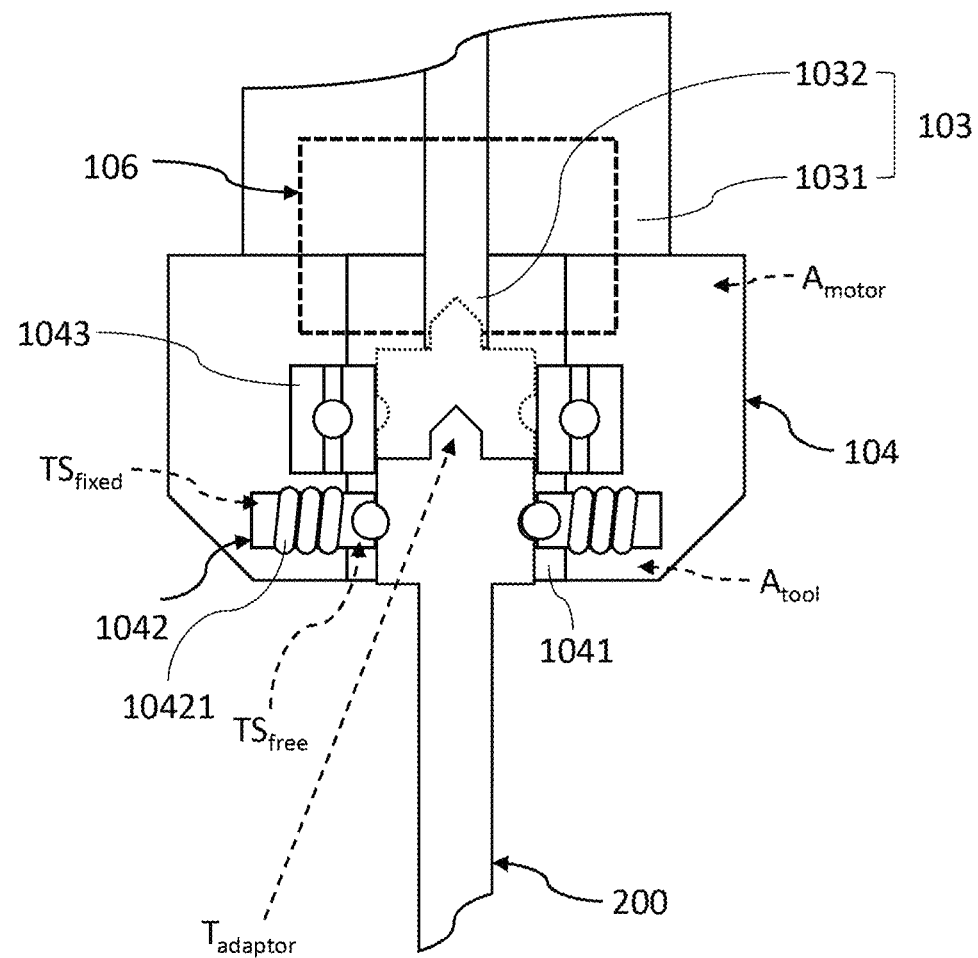
FIG. 10 illustrates a cross-sectional view around an adaptor according to one embodiment of the present disclosure.

In one embodiment of the present disclosure, the surgical device 100 further comprises an electrical leakage feedback circuit coupled to either the rotating interface 1032 or a power source end of the motor 103. In a surgical environment as shown in FIG. 1, leakage of electricity in the surgical device 100 can flow to the surgeon 1 and/or the patient 2 which is undesired. On the other hand, the leakage of electricity can also disrupt the operation of the surgical device 100 by overheating or other mal functioning. The electrical leakage feedback circuit is configured to detect leakage of electricity around the motor 103, and the tool head latchless interface 106 is further configured to stop providing attraction force when the leakage of electricity is detected by the electrical leakage feedback circuit. Upon cease of attraction force, the tool 200 is dropped by gravity. For that, the tool stopper 1042 is further configured to catch the tool 200 by the free end $TS_{free}$ within the channel 1041 after the tool 200 is dropped from the rotating interface 1032 as shown in FIG. 10. In this way, the tool stopper 1042 keeps the tool 200 in a distance from the rotating interface 1032 while holding the tool 200 within the adaptor 104. In other words, the tool 200 is isolated from the motor 103 as well as the electricity leakage.

Figure 11:
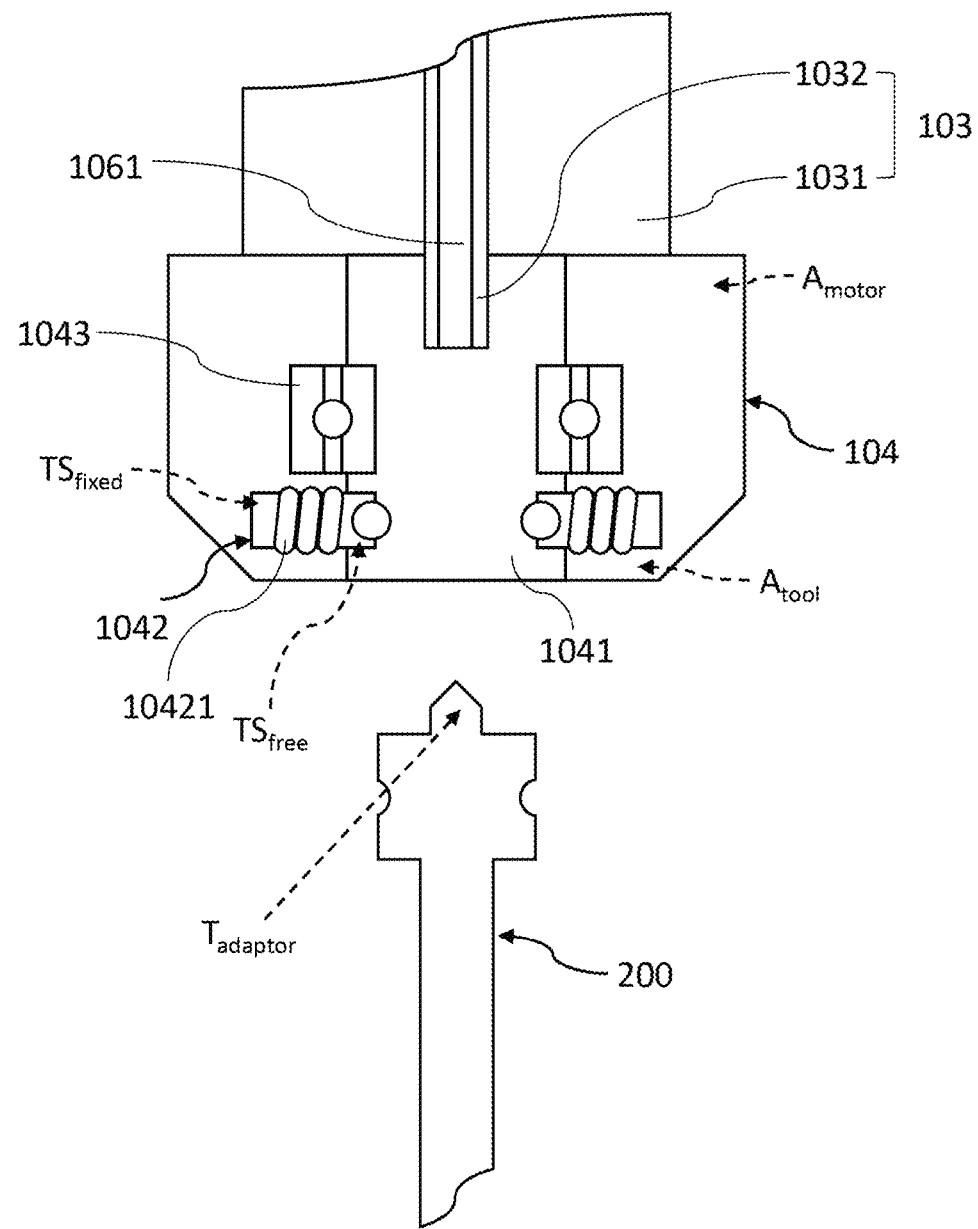
FIG. 11 illustrates a cross-sectional view around an adaptor according to one embodiment of the present disclosure.

In one embodiment of the present disclosure, the tool head latchless interface 106 comprises a gas channel 1061 extending in the rotating interface 1032 and in fluid communication with the channel 1041 of the adaptor 104 as shown in FIG. 11. As such, the gas channel 1061 is configured to allow gas passing through, and hence gas can enter or exit the adaptor 104 by flowing through the gas channel 1061 of the tool head latchless interface 106, thereby providing pressure difference. Initially, as gas exit the channel 1041 to flow into the gas channel 1061, negative pressure is created in the channel 1041, thereby attraction force provided by the tool head latchless interface 106 is generated. Therefore, a tool 200 can be pulled into the adaptor 104 and then connected to the rotating interface 1032 by attraction force. Upon connection of the tool 200, pressure in the channel 1041 returns to about atmospheric pressure (i.e. can be slightly higher or lower than atmospheric pressure), and attraction force is maintained by providing negative pressure in the gas channel 1061 of the tool head latchless interface 106, thus retaining the tool 200 to the rotating interface 1032. On the contrary, as gas enters from the gas channel 1061 into the channel 1041, positive pressure is created in the channel 1041, repulsion force provided by the tool head latchless interface 106 is generated. Therefore, a tool 200 can be pushed away from the rotating interface 1032 and out of the adaptor 104 by repulsion force.

In one embodiment of the present disclosure, the surgical device 100 further comprises a gas pump (not shown) disposed in the housing 102 and connected to the tool head latchless interface 106, the gas pump being in fluid communication with the channel 1041 of the adaptor 104 via the tool head latchless interface 106. For that, the tool head latchless interface 106 can be a gas channel in fluid communication with the channel 1041. In one embodiment, the gas channel is arranged passing through the motor 103. In another embodiment, the gas channel is arranged externally of the motor 103. The gas pump is configured to generate attraction force by providing pressure difference to the channel 1041 of the adaptor 104 via the gas channel, for example by sucking gas from the channel 1041. On the contrary, the gas pump is further configured to generate repulsion force by pumping gas from the gas channel into the channel 1041 of the adaptor 104, thereby providing pressure difference to the channel 1041. Alternatively, the gas channel can also be connected to an external pump in a surgical environment instead of the gas pump integrated in the housing 102. In this case, the fluid communication is controlled by electromechanically operated valves between the gas channel and the external pump, and the electromechanically operated valves can be disposed in the housing 102. Therefore, overall weight of the surgical device 100 can be reduced.

Figure 12:
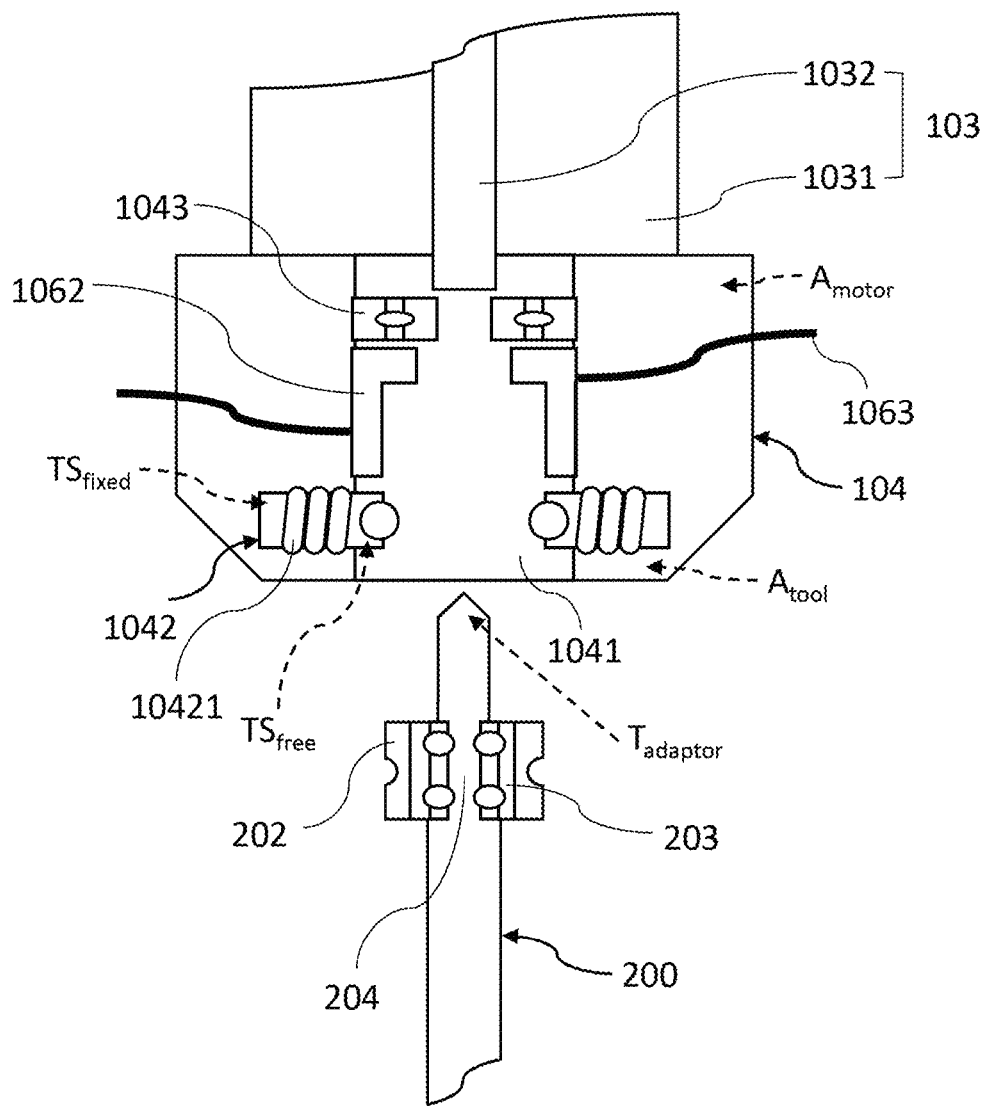
FIG. 12 illustrates a cross-sectional view around an adaptor according to one embodiment of the present disclosure.

In one embodiment of the present disclosure, the tool head latchless interface 106 comprises an electromagnet 1062 configured to generate attraction force and repulsion force by electromagnetism as shown in FIG. 12. The electromagnet 1062 is arranged between the motor 103 and the tool end $A_{tool}$ of the adaptor 104 and exposed to the channel 1041. In order to react to attraction force and repulsion force generated by electromagnetism, the tool 200 comprises a permanent magnet 202 connected thereon. The permanent magnet 202 is arranged closer to the adaptor end $T_{adaptor}$ than to the surgical end $T_{surgical}$ of the tool 200. To generate attraction force and repulsion force, the electromagnet 1062 is configured to be actuated by providing electricity thereto via cables 1063. Attraction force is generated by actuating the electromagnet 1062 in different magnetic polarity to the permanent magnet 202 of the tool 200. In the contrary, repulsion force is generated by actuating the electromagnet 1062 in same magnetic polarity to the permanent magnet 202 of the tool 200. In one embodiment, the electromagnet 1062 is arranged within the channel 1041 but not in touch with the rotating interface 1032, so rotation of the rotating interface 1032 is not counteracted by friction from the electromagnet 1062 that does not rotate along. In this case, the tool 200 further comprises a magnet bearing 203 disposed between the permanent magnet 202 and a tool body 204. Therefore, the tool body 204 is configured to rotate freely with the rotating interface 1032 while the permanent magnet 202 is retained to the electromagnet 1062 by attraction force. In another embodiment, the electromagnet 1062 is integrated to the rotating interface 1032, thus rotating with the rotating interface 1032. As such, the permanent magnet 202 and the tool body 204 both are configured to rotate with the rotating interface 1032 and the electromagnet 1062. In other words, the magnet bearing 203 is not required between the permanent magnet 202 and the tool body 204.

Figure 13:
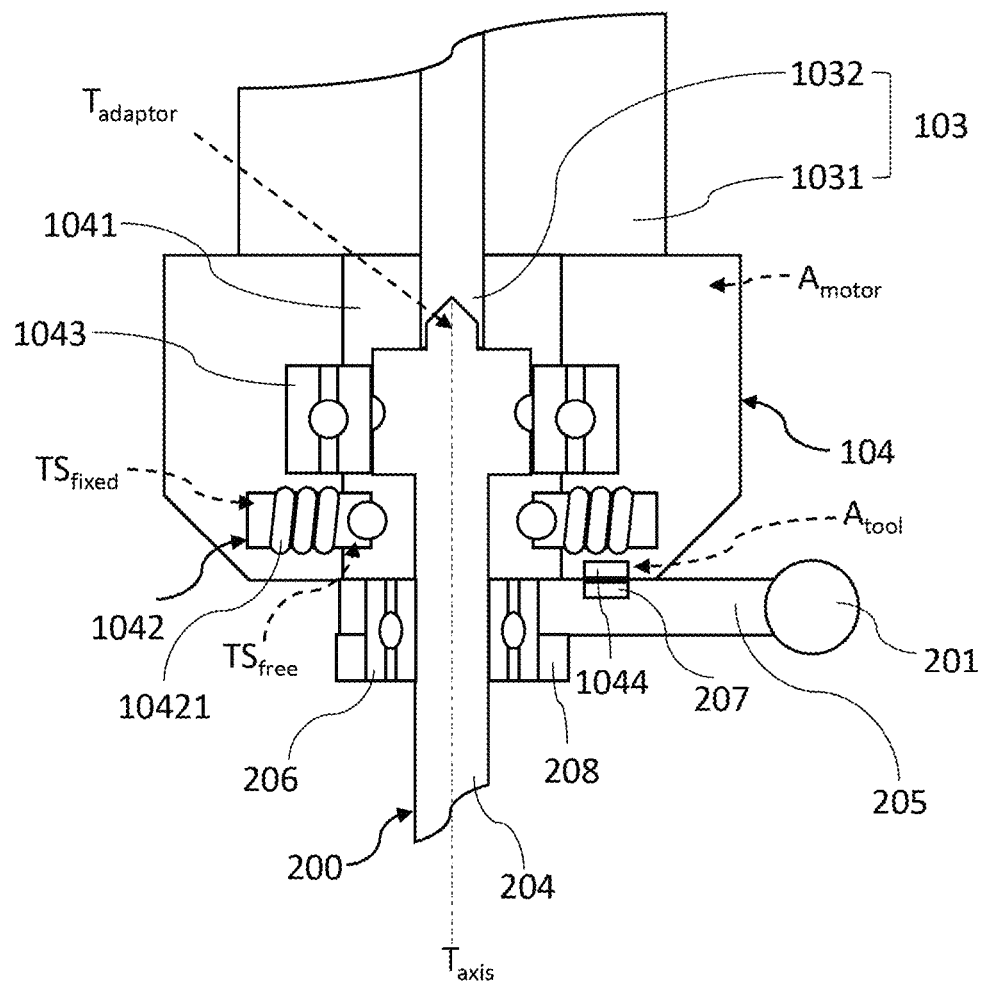
FIG. 13 illustrates a cross-sectional view around an adaptor according to one embodiment of the present disclosure.

As mentioned before, the tool marker 201 can be disposed coaxially to the tool 200 as shown in FIG. 2. In another embodiment as shown in FIG. 13, the tool marker 201 is arranged on a marker support 205 of the tool 200. The tool 200 comprises a marker bearing 206 and the marker support 205 arranged between the marker bearing 206 and the tool body 204, and both have a rotational axis coincided with the tool axis $T_{axis}$. With the help of the marker bearing 206, the marker support 205 and the tool marker 201 thereon will not rotate with the tool body 204 driven by the rotating interface 1032, which is beneficial to the tool 200 in terms of rotating stability and tracking. More specifically, a tool marker 201 not rotating with the tool body 204 will not exert undesired centrifugal force to the tool 200. And of course, it is easier to track the tool 200 by the tracker 4 according to the tool marker 201 which does not move in surgical operation. The marker support 205 can be disposed nearer the adaptor end $T_{adaptor}$ of the tool than the surgical end $T_{surgical}$ of the tool. In addition, the adaptor 104 comprises a first connector 1044 arranged at the tool end $A_{tool}$ of the adaptor 104, and the tool 200 further comprises a second connector 207 arranged on the marker support 205 between the tool marker 201 and the marker bearing 206. Therefore, the marker support 205 can be fixed to the adaptor 104 by connecting the second connector 207 to the first connector 1044. By doing so, the tool marker 201 and the marker support 205 are further prevented from rotating freely with gravity about the tool body 204. In other words, when the tool 200 is not vertical to the ground during surgical operation, the tool marker 201 will not be moved by gravity, because the marker support 205 is fixed to the surgical device 100. In one embodiment, one of the first connector 1044 and the second connector 207 is a magnet while the other one being ferromagnetic.

Figure 14:
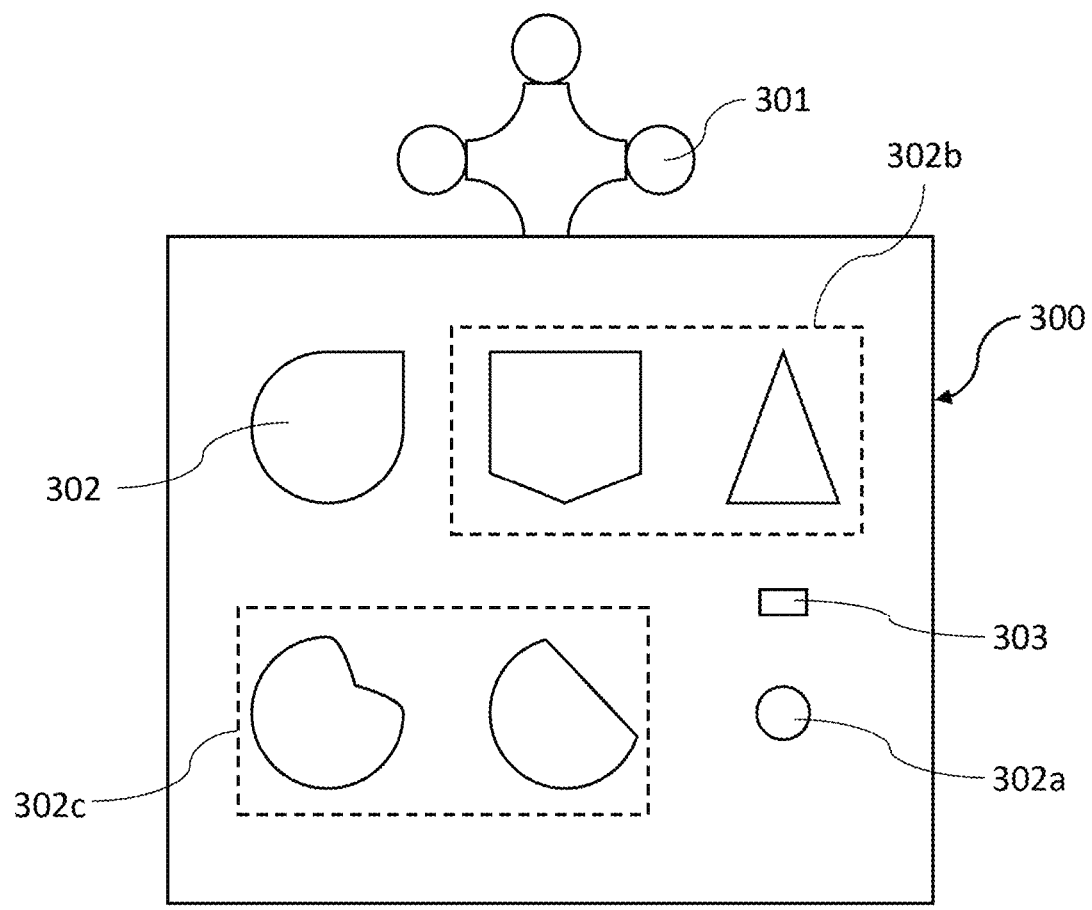
FIG. 14 illustrates a top view of a tool box according to one embodiment of the present disclosure.

In one embodiment, the tool 200 further comprises a first directional feature 208 disposed around the marker bearing 206 and fixed below the marker support 205 as shown in FIG. 13, and therefore the first directional feature 208 does not rotate with the tool body 204 as well. The first directional feature 208 have a cross-sectional shape that is directional when viewed along the tool axis $T_{axis}$. In other words, the cross-sectional shape of the first directional feature 208 does not overlap with itself more than once if it is rotated 360 degrees, i.e., lack of rotational symmetry. In FIG. 14, a tool box 300 comprising a plurality of directional tool slots 302 is shown. The first directional feature 208 is configured to be fitted into one directional tool slot 302, which is corresponding to the first directional feature 208 in shape, of the tool box 300. As such, the relative orientation between the marker support 205 and the tool box 300 can be restricted by matching the first directional feature 208 fixed to the marker support 205 to the directional tool slot 302. In another embodiment, the tool box 300 further comprises a uni-directional tool slot 302a and a third connector 303 configured to fix the marker support 205 when the tool 200 is disposed in the uni-directional tool slot 302a without the first directional feature 208. For example, the third connector 303 can be a magnet while the marker support 205 being ferromagnetic. Therefore, the relative orientation between the marker support 205 and the tool body 204 can be restricted by the tool box 300. In this way, during the process of picking up the tool 200 from the tool box 300 or returning the tool 200 to the tool box 300 by the surgical device 100, the marker support 205 is either fixed to the tool box 300 or the surgical device 100 by the third connector 303 or the first connector 1044, respectively.

In one embodiment, the tool box 300 further comprises a box marker 301 fixed thereto. The box marker 301 is a fiducial marker that can be tracked by the tracker 4 just like the device marker 105 and the tool marker 201, so the position of the tool box 300 can be known in a surgical environment. In this way, the surgical device 100 can be moved by the robotic arm 5 to the top of the tool box 300 by navigation of the surgical computer 3, thereby facilitating mounting or dismounting the tool 200.

Figure 15:
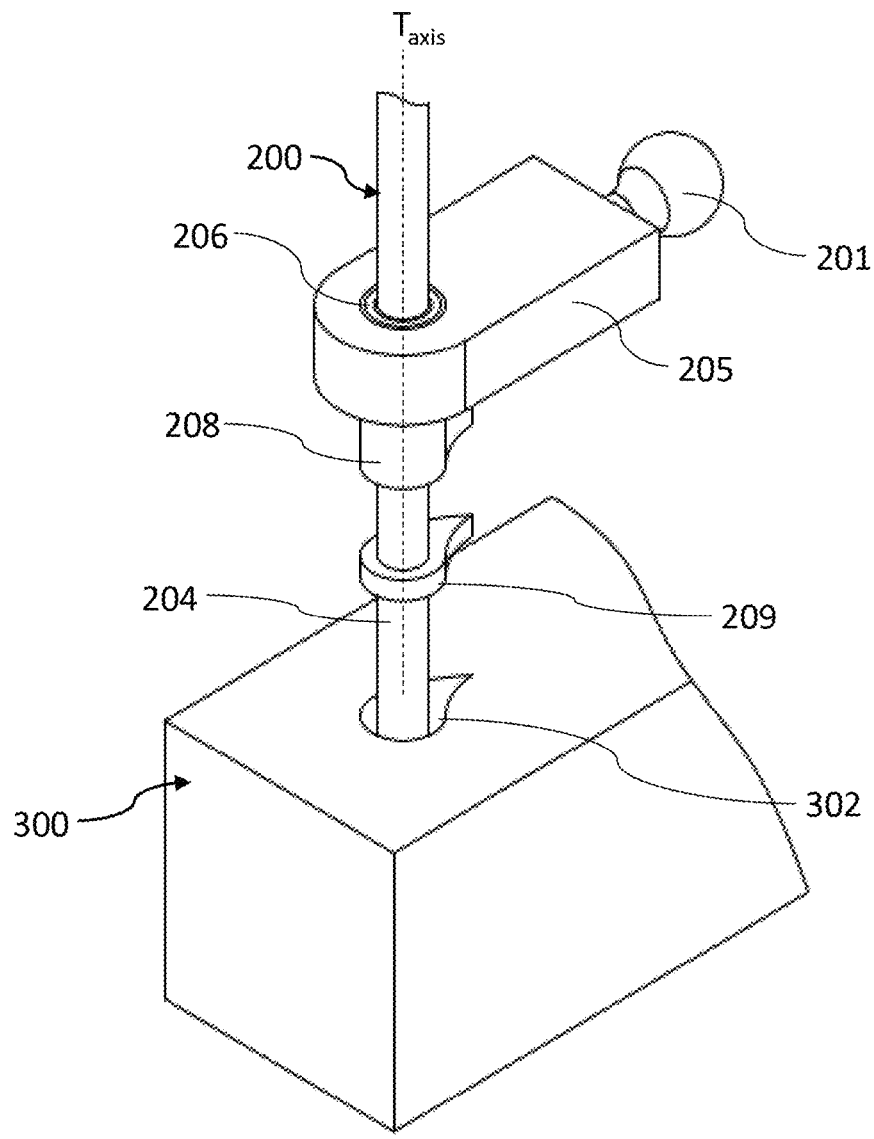
FIG. 15 illustrates an isometric view of a tool and a tool box according to one embodiment of the present disclosure.

In one embodiment, the tool 200 further comprises a second directional feature 209 fixed below the first directional feature 208 on the tool body 204 shown in FIG. 15, and the second directional feature 209 have the same cross-sectional shape as the first directional feature 208 when viewed along the tool axis $T_{axis}$, hence lack of rotational symmetry. As aforementioned, the adaptor end $T_{adaptor}$ of the tool 200 comprises at least two faces that are structurally complementary to the rotating interface 1032. In other words, the tool 200 can only be mounted to the surgical device 100 properly when the adaptor end $T_{adaptor}$ is structurally matching to the rotating interface 1032. When the tool 200 is disposed in the tool box 300, both the first directional feature 208 and the second directional feature 209 should be fitted within the directional tool slot 302. In addition, the motor 103 is configured to rotate the tool body 204 to align the cross-sectional shape of the second directional feature 209 to the first directional feature 208, in which the cross-sectional shape is defined by viewing along the tool axis $T_{axis}$. In this way, the cross-sectional shape of the adaptor end $T_{adaptor}$ can be restricted to a specific orientation by the directional tool slot 302 when viewed along the tool axis $T_{axis}$. Therefore, automatically mounting the tool 200 to the surgical device 100 can be realized by setting a default orientation to the rotating interface 1032, wherein the rotating interface 1032 at the default orientation has its cross-sectional shape overlapping the cross-sectional shape of the adaptor end $T_{adaptor}$ when viewed along the tool axis $T_{axis}$.

It should be noted that, since the first directional feature 208, the second directional feature 209, and the directional tool slot 302 should have the same cross-sectional shape, various cross-sectional shapes thereof, which is directional, will be exemplified in FIG. 14 with directional tool slots 302b and directional tool slots 302c. In one embodiment of the present disclosure, a directional shape is a non-regular polygon shape as shown by directional tool slots 302b. In another embodiment of the present disclosure, a directional shape is a non-polygon shape as shown by directional tool slots 302c.

Figure 16:
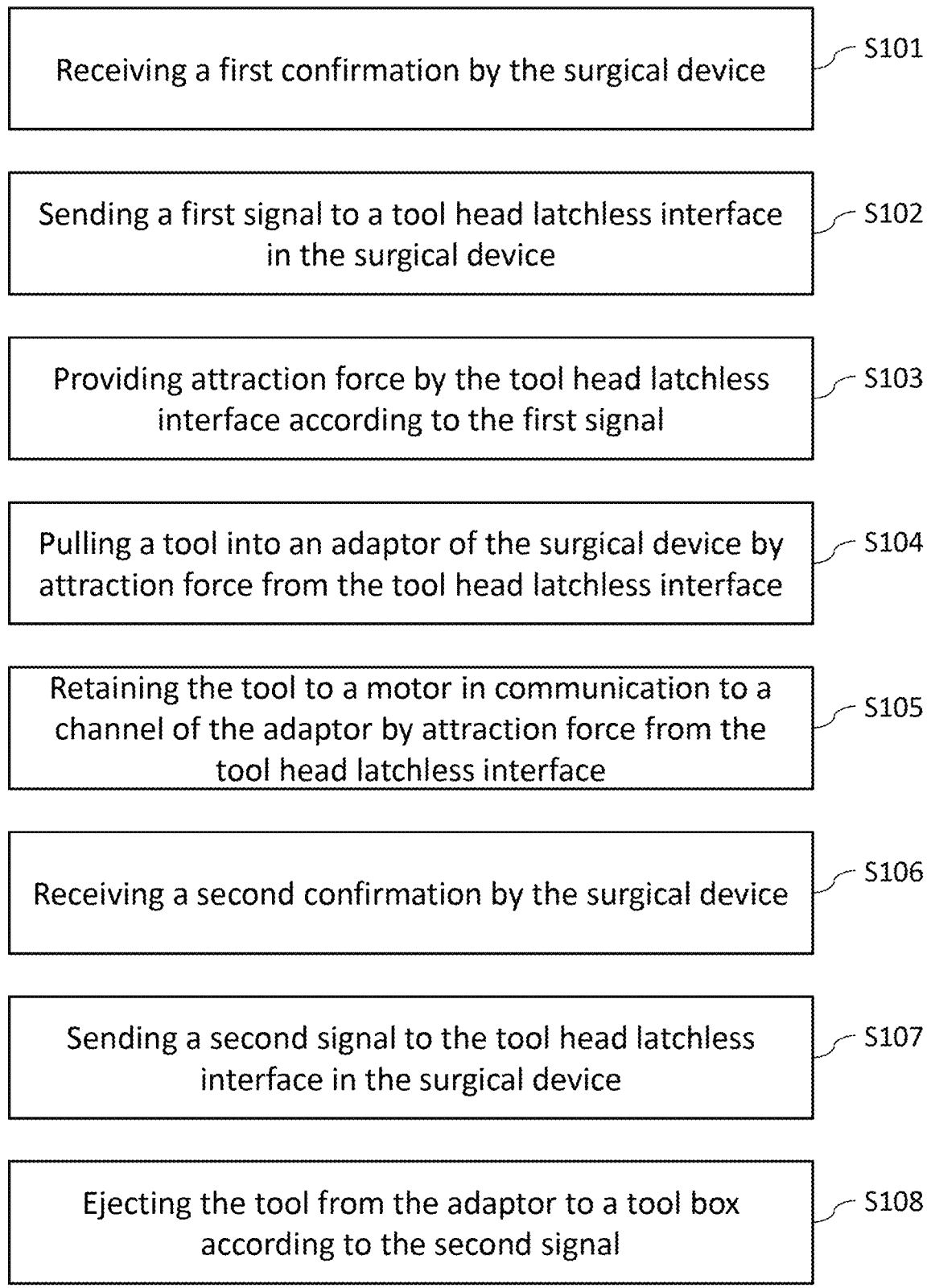
FIG. 16 shows a method of a surgical device according to one embodiment of the present disclosure.

FIG. 16 shows a method of mounting and dismounting a tool 200 by a surgical device 100 according to one embodiment of the present disclosure. The method comprises the following:

In S101, receiving a first confirmation by the surgical device 100. The first confirmation can be sent by the surgical computer 3 to the surgical device 100. In one embodiment, the first confirmation is sent when an opening of the adaptor 104 of the surgical device 100 is in proximity to the adaptor end $T_{adaptor}$ of the tool 200 disposed in the tool box 300 and when a rotational axis of the motor 103 is aligned with the tool axis $T_{axis}$. At the same time, the surgical computer 3 is configured to determine a first spatial pattern formed either by a combination of at least a device marker 105 and a tool marker 201 or by a combination of at least a device marker 105 and at least a box marker 301.

In S102, sending a first signal to a tool head latchless interface 106 in the surgical device 100. In one embodiment, the first signal is sent by a controller of the surgical device 100 to the tool head latchless interface 106 after the first confirmation is received by the surgical device 100.

In one embodiment, the controller can be disposed in the housing 102 for controlling the movement of the multi-axis manipulator 101, rotation of the motor 103, and actuation of the tool head latchless interface 106 by sending electronic signals thereto. The controller is also configured to receive feedback signal from the electrical leakage feedback circuit and then stop actuation of the tool head latchless interface 106 accordingly.

In S103, providing attraction force by the tool head latchless interface 106 according to the first signal. In one embodiment, attraction force is provided by sending a signal to actuate the pump in the housing 102 for allowing the gas channel 1061 to provide a pressure difference to the channel 1041, for example by removing gas from the channel 1041. In another embodiment, attraction force is provided by sending a signal to actuate the electromagnet 1062 to have different magnetic polarity to the permanent magnet 202 on the tool 200.

In S104, pulling the tool 200 into the adaptor 104 of the surgical device 100 by attraction force from the tool head latchless interface 106. In one embodiment, the tool 200 is pulled into the adaptor 104 by negative pressure created in the channel 1041. In another embodiment, the tool 200 is pulled into the adaptor 104 by electromagnetic force.

In S105, retaining the tool 200 to a motor 103 in communication to a channel 1041 of the adaptor 104 by attraction force from the tool head latchless interface 106. In one embodiment, the tool head latchless interface 106 provides negative pressure to the channel 1041 continuously to keep the adaptor end $T_{adaptor}$ attached to the rotating interface 1032. In another embodiment, the tool head latchless interface 106 provides electromagnetic force to the channel 1041 continuously to keep the adaptor end $T_{adaptor}$ attached to the rotating interface 1032.

In S106, receiving a second confirmation by the surgical device 100. The second confirmation can be sent by the surgical computer 3 to the surgical device 100. In one embodiment, the second confirmation is sent when the surgical end $T_{surgical}$ of the tool 200 is in proximity to an opening of the tool slot of the tool box 300 and when the tool axis $T_{axis}$ is aligned with a slot axis of the tool slot. The slot axis is defined overlapping with the tool axis $T_{axis}$ when the tool 200 is disposed in the tool slot. At the same time, the surgical computer 3 is configured to determine a second spatial pattern formed either by a combination of at least a box marker 301 and a tool marker 201 or by a combination of at least a device marker 105 and at least a box marker 301.

In S107, sending a second signal to the tool head latchless interface 106 in the surgical device 100. In one embodiment, the second signal is sent by the controller of the surgical device 100 to the tool head latchless interface 106 after the second confirmation is received by the surgical device 100.

In S108, ejecting the tool 200 from the adaptor 104 to a tool box 300 according to the second signal. In one embodiment, the tool 200 is ejected from the adaptor 104 by providing repulsion force via the tool head latchless interface 106, and repulsion force can be provided by pressure difference or electromagnetic force in the channel 1041. In another embodiment, the tool 200 is ejected from the adaptor 104 by stop providing attraction force via the tool head latchless interface 106 and dropping the tool 200 into the tool box 300 by gravity.

FIG. 17 shows a method of dismounting a tool 200 that is already in a surgical device 100 according to one embodiment of the present disclosure. The method comprises the following:

In S201, receiving a third confirmation by the surgical device 100. The third confirmation can be sent by the surgical computer 3 to the surgical device 100. In one embodiment, the third confirmation is sent when the surgical end $T_{surgical}$ of the tool 200 is in proximity to an opening of the tool slot of the tool box 300 and when the tool axis $T_{axis}$ is aligned with a slot axis of the tool slot. The slot axis is defined overlapping with the tool axis $T_{axis}$ when the tool 200 is disposed in the tool slot. At the same time, the surgical computer 3 is configured to determine a second spatial pattern formed either by a combination of at least a box marker 301 and a tool marker 201 or by a combination of at least a device marker 105 and at least a box marker 301.

In S202, sending a third signal to a tool head latchless interface 106 in the surgical device 100. In one embodiment, the third signal is sent by the controller of the surgical device 100 to the tool head latchless interface 106 after the third confirmation is received by the surgical device 100.

In S203, providing repulsion force by the tool head latchless interface according to the third signal. In one embodiment, repulsion force is provided by sending a signal to actuate the pump in the housing 102 for allowing the gas channel 1061 to provide gas into the channel 1041. In another embodiment, repulsion force is provided by sending a signal to actuate the electromagnet 1062 to have same magnetic polarity to the permanent magnet 202 on the tool 200.

In S204, moving a tool 200 over a tool stopper 1042 in a channel 1041 of an adaptor 104 of the surgical device 100 by repulsion force from the tool head latchless interface 106. In one embodiment, a free end $TS_{free}$ of the tool stopper 1042 is urged toward a fixed end $TS_{fixed}$ of the tool stopper 1042 by the tool 200 when the tool 200 passes over the tool stopper 1042, thereby allowing the tool 200 to move over the tool stopper 1042.

In S205, ejecting the tool 200 from the channel 1041 of the adaptor 104 to a tool box 300 by repulsion force from the tool head latchless interface 106.

FIG. 18 shows a method of a surgical device 100 responding to leakage of electricity according to one embodiment of the present disclosure. The method comprises the following:

In S301, detecting leakage of electricity by an electrical leakage feedback circuit in the surgical device 100. In one embodiment, the electrical leakage feedback circuit is connected to either the rotating interface 1032 or a power source end of the motor 103. In addition, the electrical leakage feedback circuit is configured to send a feedback signal to the controller disposed in the housing 102.

In S302, sending a fourth signal to a tool head latchless interface 106 that is providing attraction force in a channel 1041 of an adaptor 104 of the surgical device 100 after detection of leakage of electricity. The fourth signal is sent by the controller according to the feedback signal sent thereto by the electrical leakage feedback circuit.

In S303, stop providing attraction force in the channel 1041 by the tool head latchless interface 106 according to the fourth signal. As attraction force not being provided, the tool 200 is dropped from the tool head latchless interface 106 by gravity, thus separating the adaptor end $T_{adaptor}$ from the rotating interface 1032.

In S304, catching a tool 200 dropping from a motor 106 after cease of attraction force by a tool stopper 1042 in the channel 1041. In one embodiment, the tool 200 comprises a notch facing toward an inner wall of the channel 1041 and arranged between the adaptor end $T_{adaptor}$ and the surgical end $T_{surgical}$, and the tool stopper 1042 is configured to hold the tool 200 by having its free end $TS_{free}$ in the notch.

In S305, sending a fifth signal to the tool head latchless interface 106 after leakage of electricity is not detected by the electrical leakage feedback circuit. In one embodiment, the fifth signal is sent by the controller of the surgical device 100 to the tool head latchless interface 106 after the leakage of electricity is no longer detected.

In S306, providing attraction force by the tool head latchless interface 106 according to the fifth signal. In one embodiment, attraction force is provided by sending a signal to actuate the pump in the housing 102 for providing pressure difference in the channel 1041 via the gas channel 1061, for example by removing gas from the channel 1041. In another embodiment, attraction force is provided by sending a signal to actuate the electromagnet 1062 to have different magnetic polarity to the permanent magnet 202 on the tool 200.

In S307, pulling the tool 200 from the tool stopper 1042 toward the motor 103 and retaining the tool 200 to the motor 103 by attraction force from the tool head latchless interface 106. As the tool head latchless interface 106 providing attraction force, the tool 200 urges the tool stopper 1042 and slip over the tool stopper 1042. In consequence, the adaptor end $T_{adaptor}$ of the tool 200 moves toward the rotating interface 1032 of the motor 103 and then attach thereto. By continuously providing attraction force, the adaptor end $T_{adaptor}$ is retained to the rotating interface 1032 for conducting surgical operation.

Figure 19:
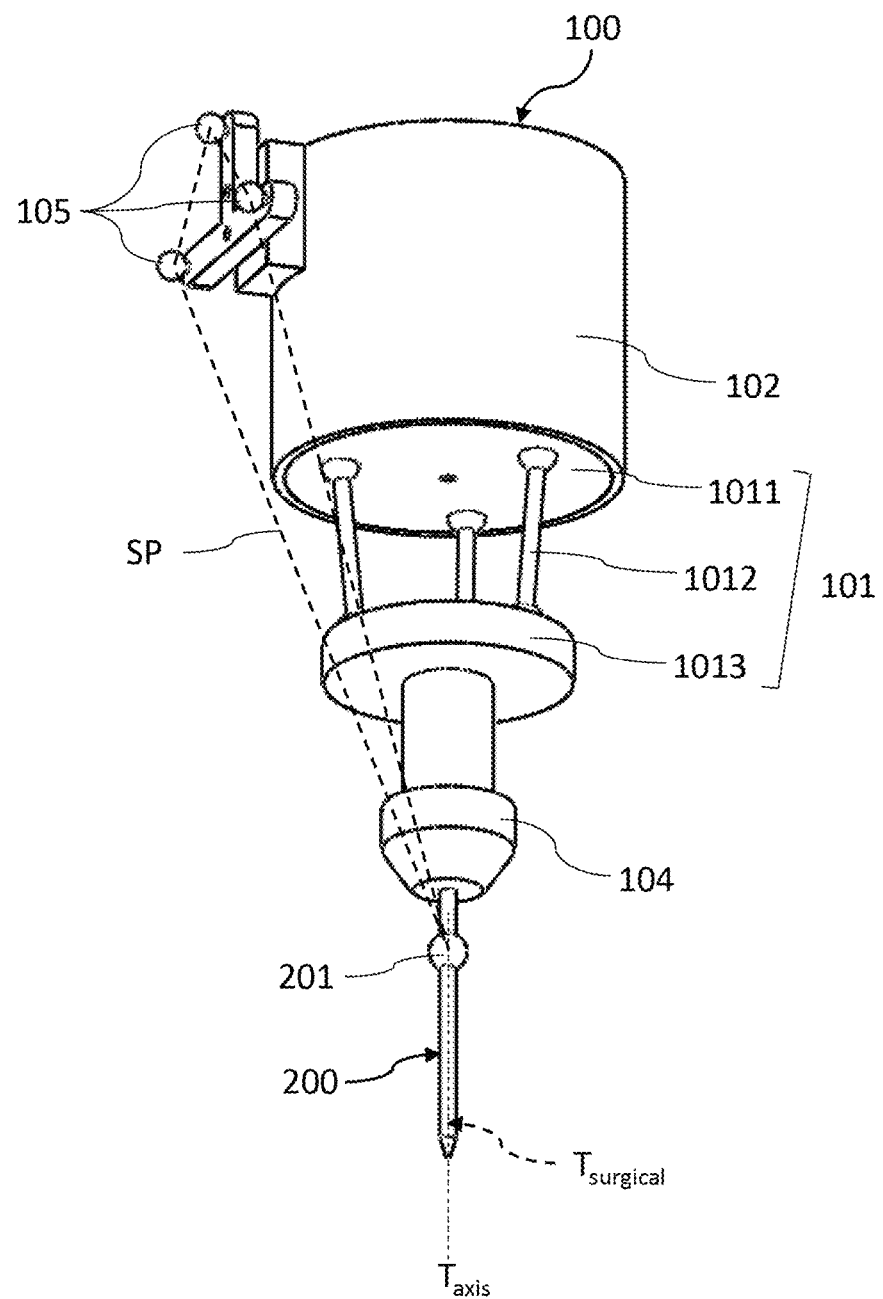
FIG. 19 illustrates an isometric view of a surgical device having a spatial pattern SP according to one embodiment of the present disclosure.
Figure 20:
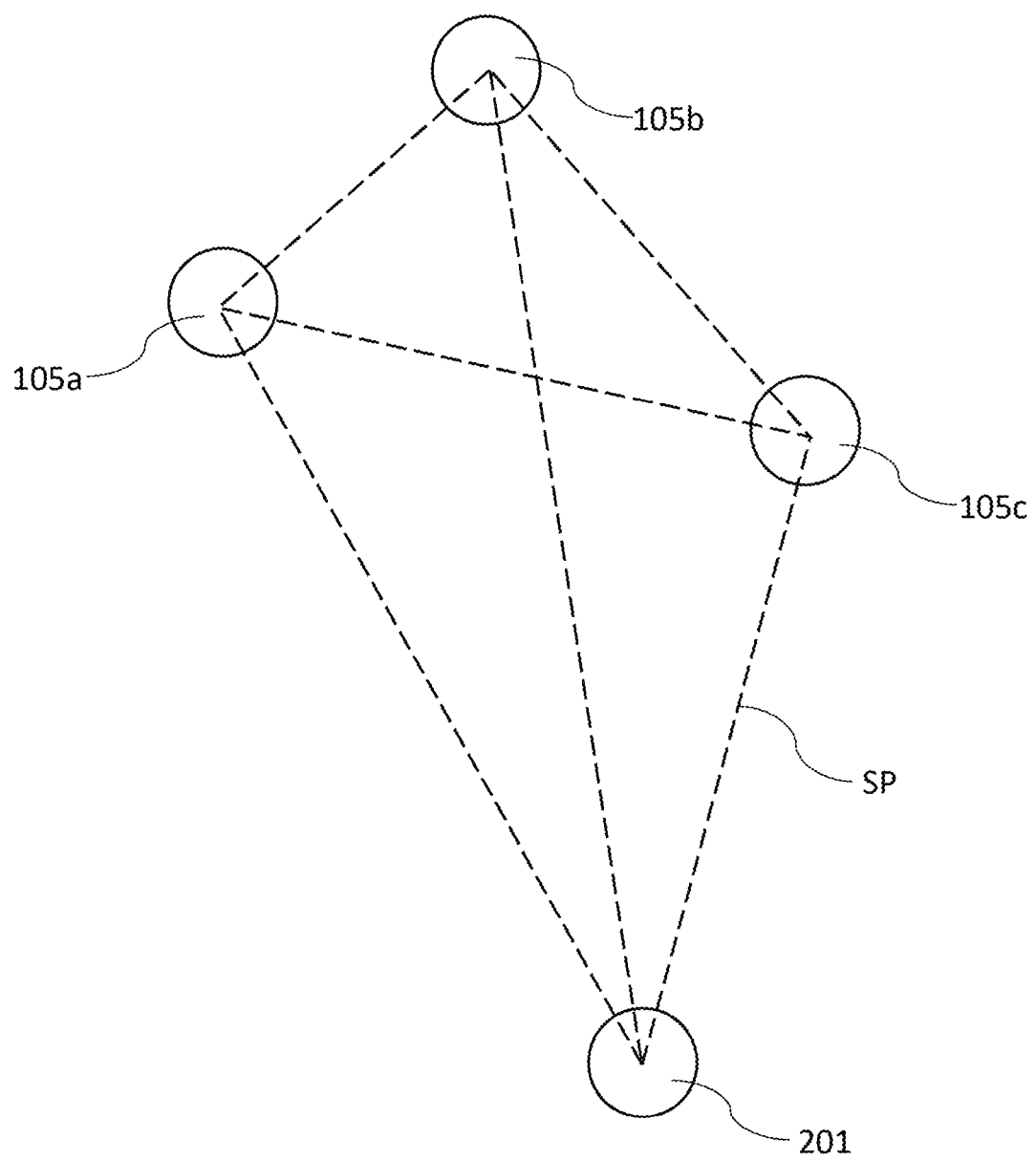
FIG. 20 shows the spatial pattern SP in FIG. 19 in a simplified view for clarity of visual illustration.
Figure 21:
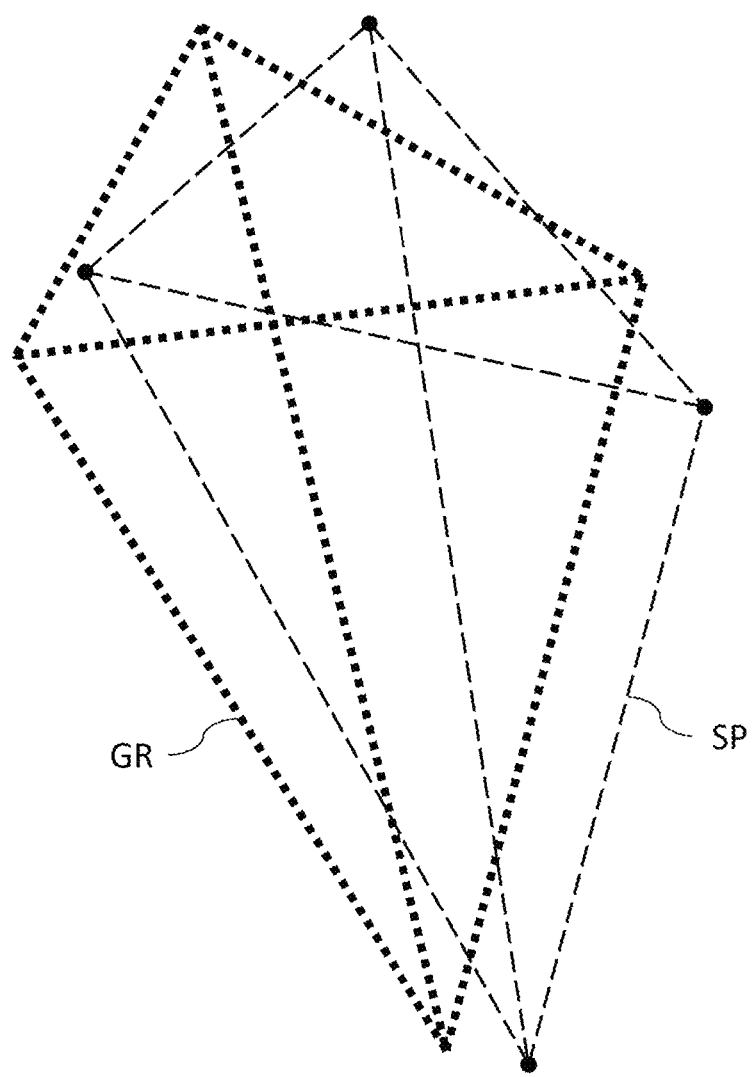
FIG. 21 shows an exaggerated deviation between a geometric relationship GR and the spatial pattern SP according to one embodiment of the present disclosure.

In FIG. 19 to FIG. 21, a macro calibration operation between the surgical device 100 and the tool 200 using spatial pattern SP and geometric relationship GR is described according to one embodiment of the present disclosure. The macro calibration may be used to ensure proper mounting of the tool 200 to the surgical device 100. FIG. 19 illustrates a spatial pattern SP formed by a plurality of device markers 105 and a tool marker 201 according to one embodiment of the present disclosure. FIG. 20 illustrates the spatial pattern SP in FIG. 19 in a simplified view for clarity of visual illustration. FIG. 21 shows the spatial pattern SP and the geometric relationship GR according to one embodiment of the present disclosure. In one embodiment, a tracker device (e.g., tracker 4 as shown in FIG. 1) is configured to obtain optical signals from the plurality of device markers 105a to 105c and the tool marker 201. The tracker device may then enable the generation of a plurality of coordinates (e.g. cartesian coordinates, cylindrical coordinates, spherical coordinates) corresponding to the markers' observed position according to the optical signals received. For example, the device marker 105a may be assigned a coordinate of $(X_1, Y_1, Z_1)$; likewise, the device marker 105b has a coordinate of $(X_2, Y_2, Z_2)$; the device marker 105c has a coordinate of $(X_3, Y_3, Z_3)$; the tool marker 201 has a coordinate of $(X_4, Y_4, Z_4)$. Moreover, the coordinates $(X_1, Y_1, Z_1)$, $(X_2, Y_2, Z_2)$, $(X_3, Y_3, Z_3)$, and $(X_4, Y_4, Z_4)$ cooperatively represent the spatial pattern SP formed between the markers.

A three dimensional (3D) geometric relationship GR (as illustrated in FIG. 21) representing proper retention of the tool 200 to the rotating interface 1032 can be saved in the surgical computer 3 (as shown in FIG. 1). As such, the coordinates of the observed spatial pattern SP by the tracker 4 can be sent to the surgical computer 3 for comparison (with the 3D geometric relationship GR). The surgical computer 3 is configured to determine whether the tool 200 is properly mounted to the surgical device 100 based on the compassion. For instance, when the coordinates of the spatial pattern SP do not match the 3D geometric relationship GR as shown in FIG. 21, the surgical computer 3 would deem the tool 200 not being properly mounted to the surgical device 100.

It should be noted that FIG. 21 shows an exaggerated deviation between the 3D geometric relationship GR and the coordinates of the spatial pattern SP just for clarity of visual illustration. In practice, the deviation between the 3D geometric relationship GR and the coordinates of the spatial pattern SP can be as small as the detection limitation of the tracker 4. It is a fact that every tracker device has a default resolution that decides how small a movement of one marker can be detected. Accordingly, the detection limitation can be defined by a smallest movement that one tracker device can detect, for example about 0.3 mm. In other words, moving either the device marker 105 or the tool marker 201 by a distance less than the detection limitation is not detectable to the tracker 4. However, movement of any marker not detected by one tracker can cause inaccuracy during a surgery. For example, a 0.1 mm deviation of the tool marker 201 can be noticeable deviation at the surgical end $T_{surgical}$ of the tool 200. Therefore, a micro calibration operation of individual markers (e.g. tool marker 201, device markers 105a, 105b, and 105c) according to acceptance area may be conducted to ensure position of each marker is at the center of the coordinate assigned thereto. As such, accuracy of mounting between the surgical device 100 and the tool 200 (as well as accuracy of a surgical operation) can be further improved.

Figure 22:
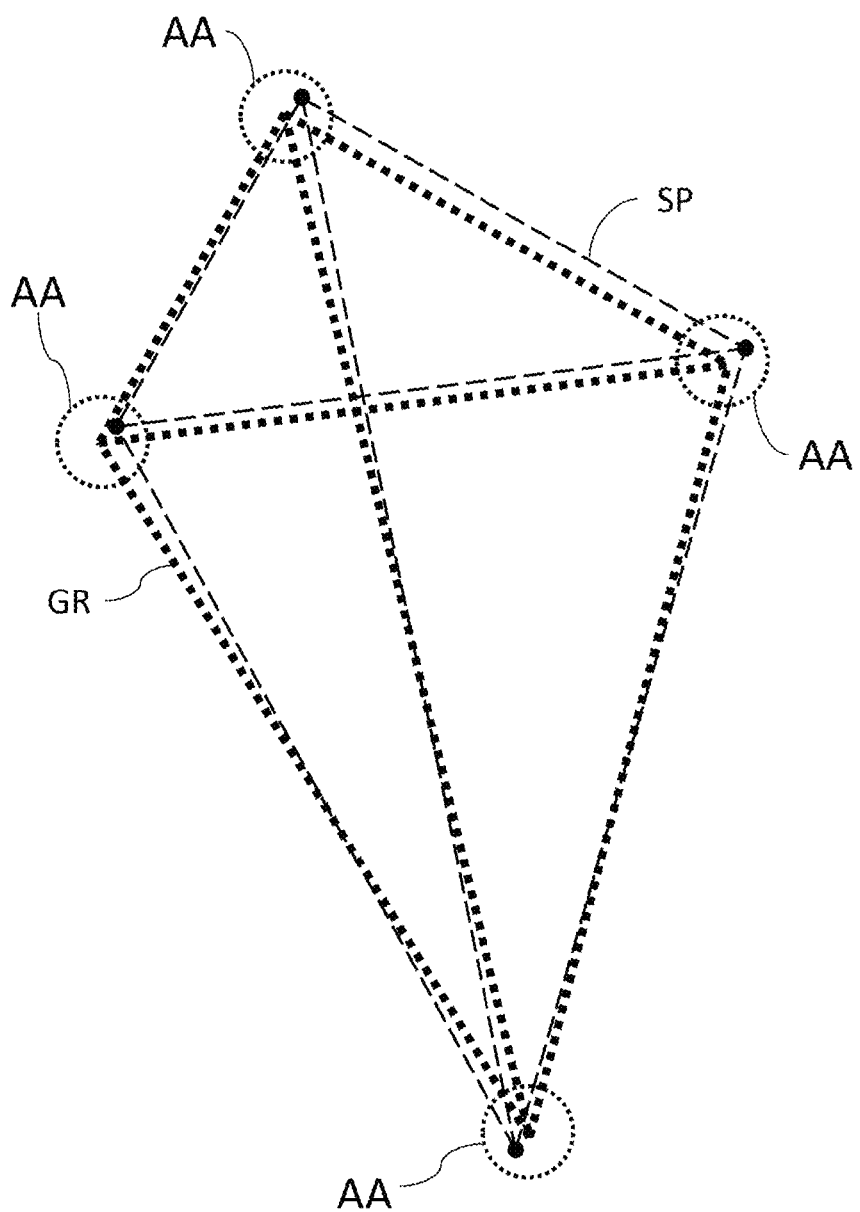
FIG. 22 shows a spatial pattern SP almost matching a geometric relationship GR according to one embodiment of the present disclosure.
Figure 23:
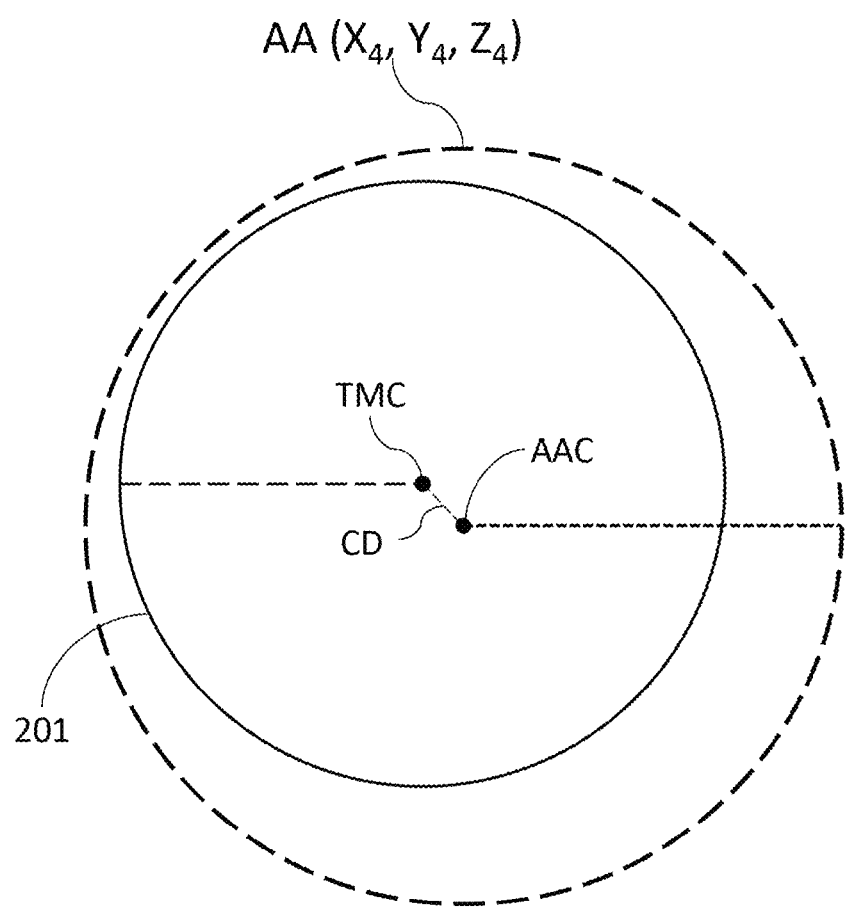
FIG. 23 shows a marker within an acceptance area AA according to one embodiment of the present disclosure.

In FIG. 22 and FIG. 23, the micro calibration is further explained. FIG. 22 illustrates the spatial pattern SP almost but not exactly matching to the geometric relationship GR according to one embodiment of the present disclosure. In this case, the tool 200 is determined properly mounted to the surgical device 100 because all coordinates of the spatial pattern SP correspondingly fall within a plurality of acceptance area AA, in which the determination is not as accurate as desired. FIG. 23 shows a marker within an acceptance area AA according to one embodiment of the present disclosure. In one embodiment of the present disclosure, the surgical computer 3 is configured to define one acceptance area AA for each coordinate in the coordinate system (i.e. cartesian coordinate system) of the tracker 4, and one marker in the acceptance area AA may be recognized by the tracker 4 with a corresponding coordinate assigned thereto by the surgical computer 3. For example, as shown in FIG. 23, the tool marker 201 within the acceptance area AA $(X_4, Y_4, Z_4)$ can be assigned with the coordinate $(X_4, Y_4, Z_4)$.

In one embodiment, the acceptance area AA $(X_4, Y_4, Z_4)$ is a sphere, and a radius thereof is defined by a sum of the detection limitation and the radius of the tool marker 201. As aforementioned, the tracker 4 is not able to detect a movement of the tool marker 201 as long as it stays within the acceptance area AA $(X_4, Y_4, Z_4)$ due to the detection limitation, i.e. coordinate thereof is not altered or reassigned. Accordingly, an exact position of the tool marker 201 within one acceptance area AA (for example AA $(X_4, Y_4, Z_4)$) cannot be recognized by the tracker 4. In this case, the micro calibration can be conducted by the surgical device 100. In one embodiment, the surgical device 100 is configured to calibrate the position of the tool marker 201 within the acceptance area AA $(X_4, Y_4, Z_4)$ by the multi-axis manipulator 101. More specifically, the position of the tool marker 201 can be calibrated by moving a tool marker center TMC of the tool marker 201 to coincide with an acceptance area center AAC. A vector that the tool marker center TMC have to move to coincide the acceptance area center AAC is called a center deviation CD, which is defined by the direct distance and direction therebetween. The center deviation CD can be determined by the surgical computer 3. In one embodiment, the center deviation CD is determined as follows:

As an example, the tool marker 201 is at an original position within one acceptance area AA under a cartesian coordinate system of the tracker 4.

The tool marker 201 is moved in a first direction (e.g. along X axis of the cartesian system) until reaching the edge of the acceptance area AA, whereby a first moving distance $D_1$ by a plurality of manipulator encoders of the multi-axis manipulator 101, and then the tool marker 201 is returned to the original position.

The tool marker 201 is moved in a second direction (e.g. along Y axis of the cartesian system) until reaching the edge of the acceptance area AA, whereby a second moving distance $D_2$ by the plurality of manipulator encoders, and then the tool marker 201 is returned to the original position.

The tool marker 201 is moved in a third direction (e.g. along Z axis of the cartesian system) until reaching the edge of the acceptance area AA, whereby a third moving distance $D_3$ by the plurality of manipulator encoders, and the tool marker 201 is returned to the original position.

It should be noted that, the first direction, the second direction, and the third direction are three different directions with known angular relationship therebetween. It should also be noted that, reaching the edge of the acceptance area AA is determined when a change to the coordinate of the tool marker 201 is detected by the tracker 4, i.e. movement of the tool marker 201 is larger than the detection limitation. For example, when the tool marker 201 moves beyond the edge of the acceptance area AA $(X_4, Y_4, Z_4)$ the coordinate of the marker 201 recognized by the tracker 4 changes from $(X_4, Y_4, Z_4)$ to a different coordinate, thus reaching the edge of the acceptance area AA $(X_4, Y_4, Z_4)$. The moving distances $D_1$, $D_2$, and $D_3$ are sent to the surgical computer 3, and the center deviation CD is determined by the surgical computer 3 using the moving distances $D_1$, $D_2$, $D_3$ and the angular relationship between the first direction, the second direction, and the third direction. Accordingly, the tool marker 201 can be moved with the center deviation CD by the multi-axis manipulator 101 so as to be at the acceptance area center AAC.

Though tool marker 201 was used as an example for explanation of micro calibration within an acceptance area, the same calibration technique can be applied to the device marker 105 as well. In one embodiment of the present disclosure, after calibrating the position of the tool marker 201 to coincide with the acceptance area center AAC, the device markers 105 of the surgical device 100 can be calibrated by moving the device markers 105 through moving the surgical device 100 with the robotic arm 5 while keeping the tool marker 201 stationary. In this case, for every movement of the device markers 105 during calibration, the multi-axis manipulator 101 moves the tool marker 201 inversely to keep the calibrated position thereof unchanged. Therefore, accuracy of automatic mounting the tool 200 to the surgical device 100 can be increased after calibration of the device marker 105 and the tool marker 201 within corresponding acceptance area thereof.

In another embodiment of the present disclosure, micro calibration of the device markers 105 can be conducted by the multi-axis manipulator 101 while the tool 200 mounted to the surgical device 100 is within the tool box 300. In this case, the position of the tool box 300 is configured to be fixed in a surgical environment, so the position of the moving end 1013 of the multi-axis manipulator 101 and the tool marker 201 can be indirectly maintained by the tool box 300. The robotic arm 5 connected to the surgical device 100 is configured to be passively moved by the stationary end 1011 of the multi-axis manipulator 101 (i.e. like a passive linkage), therefore the stationary end 1011 and the device markers 105 can be moved relatively to the moving end 1013 and the device marker 201, and micro calibration of the device markers 105 can be conducted as such. It should be noted that there is no specific order between micro calibration of the tool marker 201 and micro calibration of the device markers 105.

The embodiments shown and described above are only examples. Many details are often found in this field of art thus many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A surgical device for retaining a tool, comprising:
   a multi-axis manipulator having a stationary end and a moving end, the manipulator being configured to generate relative movement between the moving end and the stationary end;
   a housing fixed to the stationary end of the manipulator;
   a motor having a rotating interface, the motor being configured to rotate the tool by the rotating interface when the tool is retained to the rotating interface;
   an adaptor connected to the manipulator and in orientation fixation to the moving end of the manipulator, the adaptor being configured to move with the moving end, and the adaptor comprises:
   a motor end,
   a tool end,
   a tool stopper disposed between the motor end and the tool end, and
   a channel extending between the motor end and the tool end,
   wherein the channel is configured to receive the rotating interface from the motor end and to receive the tool from the tool end, and
   wherein the tool stopper has a fixed end fixed to the adaptor, a free end extending into the channel, and a resilient unit disposed between the free end and the fixed end,
   wherein the resilient unit is configured to reset the free end urged toward the fixed end,
   wherein the tool stopper is configured to catch the tool by the free end within the channel when the tool is dropped from the rotating interface;
   a tool head latchless interface exposed to the channel of the adaptor and configured to provide attraction force within the channel for retaining the tool to the rotating interface.

2. The surgical device of claim 1, wherein the tool stopper is kept distant from the tool when the tool is retained to the rotating interface.

3. The surgical device of claim 1, wherein the free end of the tool stopper comprises a roller ball being in touch with the tool when the tool is retained to the rotating interface, and wherein the roller ball is configured to rotate freely for reducing friction between the tool stopper and the tool.

4. The surgical device of claim 1, further comprises an electrical leakage feedback circuit coupled to the motor and configured to detect leakage of electricity, wherein the tool head latchless interface is further configured to stop providing attraction force upon detection of leakage by the electrical leakage feedback circuit.

5. The surgical device of claim 4, wherein the tool stopper is further configured to keep the tool isolated from the rotating interface of the motor while holding the tool within the adaptor when the leakage of electricity is detected by the electrical leakage feedback circuit.

6. The surgical device of claim 1, wherein the tool head latchless interface is further configured to provide attraction force for the tool to overcome the tool stopper, such that the tool is moved from outside to inside of the channel of the adaptor and retained over the rotating interface.

7. The surgical device of claim 1, wherein the tool head latchless interface is further configured to provide repulsion force for the tool to overcome the tool stopper, such that the tool is moved from inside to outside of the channel of the adaptor and separated from the rotating interface.

8. The surgical device of claim 1, wherein the adaptor further comprises a bearing exposed to the channel and disposed between the motor end of the adaptor and the tool stopper, configured to facilitate stable rotation of the tool.

9. The surgical device of claim 8, wherein the tool is in physical contact only with the tool head latchless interface, the rotating interface, and the bearing when the tool head latchless interface retains the tool to the rotating interface.

10. The surgical device of claim 1, wherein the tool head latchless interface comprises a gas channel extending in the rotating interface and in fluid communication with the channel of the adaptor, wherein the gas channel is configured to allow gas passage there-through, and the tool head latchless interface is further configured to provide repulsion force, and wherein attraction force and repulsion force are provided by pressure difference generated through the gas channel.

11. The surgical device of claim 1, further comprising a gas pump disposed in the housing and connected to the tool head latchless interface, the gas pump being in fluid communication with the channel of the adaptor via the tool head latchless interface, wherein the gas pump is configured to generate attraction force by sucking gas from the channel of the adaptor into the tool head latchless interface, and the gas pump is further configured to generate repulsion force by pumping gas from the tool head latchless interface into the channel of the adaptor.

12. The surgical device of claim 1, wherein the tool head latchless interface comprises an electromagnet configured to generate attraction force and repulsion force by electromagnetism, wherein attraction force is generated by having the electromagnet in different magnetic polarity to the tool, and repulsion force is generated by having the electromagnet in same magnetic polarity to the tool.

13. The surgical device of claim 1, the adaptor further comprises a connector disposed externally at the second end of the adaptor, wherein the tool comprises a marker support, and the connector is configured to connect the marker support of the tool so as to fix the marker support to the adaptor when the tool rotates with the rotating interface.

14. The surgical device of claim 13, further comprises the tool having a first end and a second end, the tool comprising:
a tool body elongating between the first end and the second end;
the marker support disposed nearer the first end of the tool than the second end of the tool; and
a marker bearing disposed between the tool body and the marker support, and the marker bearing is configured to facilitate the marker support to rotate freely about the tool body;
wherein a tool axis is defined by a rotational axis of the marker support.

15. The surgical device of claim 14, wherein the tool further comprises a first directional feature fixed to the marker support and a second directional feature fixed to the tool; wherein the first directional feature is arranged between the marker support and the second directional feature; and wherein the first directional feature and the second directional feature have the same cross-sectional shape when viewed along the tool axis.

16. The surgical device of claim 15, wherein the motor is configured to rotate the tool to align cross-sectional shape of the first directional feature to the second directional feature so as to fit both the first directional feature and the second directional feature into a directional tool slot.

17. The surgical device of claim 15, wherein the first directional feature and the second directional feature respectively comprise non-regular polygonal profiles when viewed along the tool axis.

18. The surgical device of claim 15, wherein the first directional feature and the second directional feature are of non-polygon shapes that lack rotational symmetry when viewed along the tool axis.

19. The surgical device of claim 1, further comprises the tool having a first end and a second end, and the tool comprises a fiducial marker; wherein a tool axis of the tool is defined extending between the first end and the second end; and wherein, the fiducial marker is axially symmetric to the tool axis and is coaxially connected to the tool.

20. The surgical device of claim 1, further comprises the tool having a first end and a second end, and the tool comprises a permanent magnet and a bearing connected between the tool and the permanent magnet; wherein the permanent magnet is closer to the first end of the tool than to the second end of the tool; and wherein the permanent magnet is configured to react to attraction force provided by the tool head latchless interface.

21. The surgical device of claim 1, further comprises a set of first fiducial markers and the tool, and the tool comprises a second fiducial marker, wherein the set of first fiducial markers and the second fiducial marker are configured to form a spatial pattern recognizable to an optical sensor, wherein the spatial pattern comprises a plurality of coordinates, and matching between a geometrical relationship and the plurality of coordinates of the spatial pattern represents proper retention of the tool to the rotating interface.

* * * * *